United States Patent [19]
Noguchi

[11] Patent Number: 5,873,082
[45] Date of Patent: Feb. 16, 1999

[54] LIST PROCESS SYSTEM FOR MANAGING AND PROCESSING LISTS OF DATA

[75] Inventor: Tamotsu Noguchi, Kawasaki, Japan

[73] Assignee: Fujitsu Limited, Kawasaki, Japan

[21] Appl. No.: 904,425

[22] Filed: Jul. 31, 1997

Related U.S. Application Data

[63] Continuation of Ser. No. 439,280, May 11, 1995, abandoned.

[30] Foreign Application Priority Data

Sep. 1, 1994 [JP] Japan .................................. 6-208308

[51] Int. Cl.$^6$ ...................................................... G06F 17/30
[52] U.S. Cl. ................................... 707/3; 707/4; 707/100
[58] Field of Search ...................................... 707/3, 4, 100

[56] References Cited

U.S. PATENT DOCUMENTS

| | | | |
|---|---|---|---|
| 5,220,657 | 6/1993 | Bly et al. | 395/425 |
| 5,297,249 | 3/1994 | Bernstein et al. | 395/156 |
| 5,341,293 | 8/1994 | Vertelney et al. | 364/419.17 |
| 5,530,852 | 6/1996 | Meske, Jr. et al. | 395/600 |

OTHER PUBLICATIONS

Obraczka, Danzig, and Li, "Internet Resource Discovery Services", vol. 26, No. 9, pp. 8–22, Sep. 1993.

Patent & Trademark Office, Office of Integrated Software Systems, "Microsoft Mail for Windows, A guide to using MS Mail On PTOnet" May 1993.

*Primary Examiner*—Thomas G. Black
*Assistant Examiner*—Cheryl Renea Lewis
*Attorney, Agent, or Firm*—Staas & Halsey

[57] ABSTRACT

A list storing unit stores a plurality of lists, each of which includes a plurality of data and represents a search result of a search in a database. At least a piece of the data in one of the lists is included in another one of the lists. A file name that includes information used for searching data from the database is added to each list. A feature extracting unit extracts features such as similarities and differences between the lists. A feature displaying unit displays extracted features on the screen of a terminal along with the file names. Thus, the features of the lists corresponding to the information are quickly grasped. For example, in a sequence database search, although a data amount included in the lists is huge, similarities among lists can be analyzed in a short time.

23 Claims, 33 Drawing Sheets

| CATEGORY ITEM | DESCRIPTION |
|---|---|
| SEQUENCE | GENE SEQUENCE OR AMINO ACID SEQUENCE TO BE SEARCHED |
| METHOD FOR SEQUENCE DATABASE SEARCH | METHOD FOR SEQUENCE DATABASE SEARCH SUCH AS FASTA, BLAST, SMITH-WATERMAN, ETC. |
| DATA BASE | SEQUENCE DATABASE SUCH AS GENBANK, EMBL, DDBJ, NBRF, SWISS-PORT, ETC. |
| PARAMETERS | PARAMETERS OF HOMOLOGY METHOD FOR SEQUENCE DATABASE SEARCH AFFECTING RETRIEVED RESULTS |

FIG. 2

RESULTANT FILE NAME: SEQUENCE NAME_NAME OF METHOD_DB NAME_PARAMETERS
(EXAMPLE)   HIV11_FASTA_SW_5.5.1

```
HIV__FASTA1__SW__5.2.1      LYSO__FASTA1__SW__5.2.1      UBIQ__FASTA1__SW__5.2.1
HIV__FASTA1__SW__5.5.1      LYSO__FASTAN__SW__5.2.1      UBIQ__FASTAN__SW__5.2.1
HIV__FASTAN__SW__5.2.1      LYSO__FASTA1__SW__5.5.1      UBIQ__FASTA1__SW__5.5.1
HIV__FASTAN__SW__5.5.1      LYSO__FASTAN__SW__5.5.1      UBIQ__FASTAN__SW__5.5.1
HIV__FASTAO__SW__5.2.1                ...                          ...
HIV__FASTAO__SW__5.5.1
HIV__SM-WT __SW__5.2.2      LECTIN__FASTA1__SW__5.2.1    TRYPSIN__FASTA1__SW__5.2.1
HIV__SM-WT __SW__5.5.1      LECTIN__FASTAN__SW__5.2.1    TRYPSIN__FASTAN__SW__5.2.1
          ...               LECTIN__FASTA1__SW__5.5.1    TRYPSIN__FASTA1__SW__5.5.1
                            LECTIN__FASTAN__SW__5.5.1    TRYPSIN__FASTAN__SW__5.5.1
```

Fig. 5

```
Param : DETAIL INFORMATION OF PARAMETERS IN METHOD FOR SEQUENCE DATABASE SEARCH
   (EXAMPLE)   Gap Penalty U=5, Gap Penalty V=2, ktup=1
Sequence : NAME OF TARGET SEQUENCE TO BE SEARCHED
   (EXAMPLE)   HIV-1 PROTEASE
DB : NAME OF DATABASE TO BE SEARCHED
   (EXAMPLE)   SWISS-PROT
LIST : NAME OF SEARCHED SEQUENCE (ENTRY NAME OF SEQUENCE FOR EACH DATABASE)
       AND SCORE (REPRESENTING SIMILARITIES OF SEQUENCE)
   (EXAMPLE)   HIV__MANMA    1133
               HIV__YEAST    1127
               HIV__THEP3    1018
               HIV__DESVH     999
               HIV__ECOLI     988
               HIV__SCOPO     503
               HIV__ARATH     198
               HIV__PHAAU     174
                  . . .
```

FIG. 6

|   | Ala | Arg | Asn | Asp | Cys | Gln | Glu | Gly | His | Ile | Leu | Lys | Met | Phe | Pro | Ser | Thr | Trp | Tyr | Val | Asx | Glx | ??? |
|---|---|---|---|---|---|---|---|---|---|---|---|---|---|---|---|---|---|---|---|---|---|---|---|
| A Ala | 2 |  |  |  |  |  |  |  |  |  |  |  |  |  |  |  |  |  |  |  |  |  |  |
| R Arg | -2 | 6 |  |  |  |  |  |  |  |  |  |  |  |  |  |  |  |  |  |  |  |  |  |
| N Asn | 0 | 0 | 2 |  |  |  |  |  |  |  |  |  |  |  |  |  |  |  |  |  |  |  |  |
| D Asp | 0 | -1 | 2 | 4 |  |  |  |  |  |  |  |  |  |  |  |  |  |  |  |  |  |  |  |
| C Cys | -2 | -4 | -4 | -5 | 12 |  |  |  |  |  |  |  |  |  |  |  |  |  |  |  |  |  |  |
| Q Gln | 0 | 1 | 1 | 2 | -5 | 4 |  |  |  |  |  |  |  |  |  |  |  |  |  |  |  |  |  |
| E Glu | 0 | -1 | 1 | 3 | -5 | 2 | 4 |  |  |  |  |  |  |  |  |  |  |  |  |  |  |  |  |
| G Gly | 1 | -3 | 0 | 1 | -3 | -1 | 0 | 5 |  |  |  |  |  |  |  |  |  |  |  |  |  |  |  |
| H His | -1 | 2 | 2 | 1 | -3 | 3 | 1 | -2 | 6 |  |  |  |  |  |  |  |  |  |  |  |  |  |  |
| I Ile | -1 | -2 | -2 | -2 | -2 | -2 | -2 | -3 | -2 | 5 |  |  |  |  |  |  |  |  |  |  |  |  |  |
| L Leu | -2 | -3 | -3 | -4 | -6 | -2 | -3 | -4 | -2 | 2 | 6 |  |  |  |  |  |  |  |  |  |  |  |  |
| K Lys | -1 | 3 | 1 | 0 | -5 | 1 | 0 | -2 | 0 | -2 | -3 | 5 |  |  |  |  |  |  |  |  |  |  |  |
| M Met | -1 | 0 | -2 | -3 | -5 | -1 | -2 | -3 | -2 | 2 | 4 | 0 | 6 |  |  |  |  |  |  |  |  |  |  |
| F Phe | -4 | -4 | -4 | -6 | -4 | -5 | -5 | -5 | -2 | 1 | 2 | -5 | 0 | 9 |  |  |  |  |  |  |  |  |  |
| P Pro | 1 | 0 | -1 | -1 | -3 | 0 | -1 | -1 | 0 | -2 | -3 | -1 | -2 | -5 | 6 |  |  |  |  |  |  |  |  |
| S Ser | 1 | 0 | 1 | 0 | 0 | -1 | 0 | 1 | -1 | -1 | -3 | 0 | -2 | -3 | 1 | 3 |  |  |  |  |  |  |  |
| T Thr | 1 | -1 | 0 | 0 | -2 | -1 | 0 | 0 | -1 | 0 | -2 | 0 | -1 | -3 | 0 | 1 | 3 |  |  |  |  |  |  |
| W Trp | -6 | 2 | -4 | -7 | -8 | -5 | -7 | -7 | -3 | -5 | -2 | -3 | -4 | 0 | -6 | -2 | -5 | 17 |  |  |  |  |  |
| Y Tyr | -3 | -4 | -2 | -4 | 0 | -4 | -4 | -5 | 0 | -1 | -1 | -4 | -2 | 7 | -5 | -3 | -3 | 0 | 10 |  |  |  |  |
| V Val | 0 | -2 | -2 | -2 | -2 | -2 | -2 | -1 | -2 | 4 | 2 | -2 | 2 | -1 | -1 | -1 | 0 | -6 | -2 | 4 |  |  |  |
| B Asx | 0 | -1 | 2 | 3 | -4 | 1 | 2 | 0 | 1 | -2 | -3 | 1 | -2 | -5 | -1 | 0 | 0 | -5 | -3 | -2 | 2 |  |  |
| Z Glx | 0 | 0 | 1 | 3 | -5 | 3 | 3 | 0 | 2 | -2 | -3 | 0 | -2 | -5 | 0 | 0 | -1 | -6 | -4 | -2 | 2 | 3 |  |
| X ??? | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Fig. 7

```
2CPP    --TTFGHGSHLCLGQHLARREIIVTLKEWLTRIPDFSIA-PGAQIQHKSGIVSGVQALPL
A25660  --TTFGHGSHLCLGQHLARREIIVTLKEWLTRIPDFSIA-PGAQIQHKSGIVSGVQALPL
O4PSCP  --TTFGHGSHLCLGQSLARREIIVTLKEWLTRIPDFSIA-PGAQIQHKSGIVSGVQALPL
O4BS6M  --LTFGNGPHFCLGAPLARLEMKIILEAFLEAFSHIE---PFEDFELEPHLTASATGQSL
A40401  --LGFGFGDHRCIAEHLAKAELTTVFSTLYQKFPDLKVAVPLGKINYTPLNRDVGIVD--
S18924  --LAFGFGVHQCLGQNLARAELDIAMRTLFERLPGLRLAVPAHEIRHKPGDTIQGLLD--
A35401  --LAFGFGVHQCLGQNLARLELEVILNALMDRVPTLRLAVPVEQLVLRPGTTIQGVNE--
B35401  --VAFGFGVHQCLGQPLARVELQIAIETLLRRLPDLRLAVPHEEIPFRGDMAIYGVHS--
S15809  --LAFGHGMHQCLGRQLARIELRVALTALLERFPHLRLACPAAEIPLRHDMQVYGADR--
A27555  --LAFGCGARVCLGESLARLELFVVLRLLQAF-TL-LPPPVGALPSLQPDPYCGVNLKV
A24101  --LAFGCGARVCLGECLARLELFVVLRLLQAF-TL-LPPPVGALPSLQPDPYCGVNLKV
O4BOC2  --LAFGCGARVCLGESLARLELFVVLRLLQAF-TL-LPPPVGALPSLQPDPYCGVNLKV
A27865  --LAFGCGARVCLGEPLARLELFVVLRLLQAF-TL-LPSG-DALPSLQPLPHCSVILKM
A25446  --LAFGCGARVCLGEPLARLELFVVLTRLLQAF-TL-LPSG-DALPSLQPLPHCSVILKM
O4HUC2  --LAFGCGAPVCLGEPLARLELFVVLARLLQAF-TL-LPSG-DALPSLQPLPHCSVILKM
A32306  --LGFGAGVHRCLGETLARIELQEGLRTLLRRAPN--LAVVGDWPRMGHGGIRRATDMM
A33813  GSVPFGYGVRACLGRRIAELEMQLLLARLIQRY-ELMLAPETGEVQSVARI----VLVPN
A26660  --PSFGCGARVCLGEPLARLELFVVLARLLQAF-TL-LPPPDGTLPSLQPQPYAGINLPI
A32715  --LAFGCGARVCLGEPLARLELFVVLTRLLQAF-TL-LPSG-DALPSLQPLPHCSVILKM
         *    *     *     ..       *            *  .
```

Fig. 8

```
>2CPP CYTOCHROME P450CAM (CAMPHOR MONOOXYGENASE) : 405 aa
vs pir library
search file :
    /rie/home1/pir33/pir1.dat
    /rie/home1/pir33/pir2.dat
    /rie/home1/pir33/pir3.dat
using protein matrix
```

Fig. 9

```
        initn   initl
  < 2     9     9:=====
    4     5     5:===
    6    21    21:===========
    8    68    68:==================================
   10   211   211:================================================
   12   593   593:================================================
   14   703   703:================================================
   16  1406  1406:================================================
   18  2423  2423:================================================
   20  2676  2676:================================================
   22  4318  4318:================================================
   24  6838  6838:================================================
   26  5029  5029:================================================
   28  5324  5324:================================================
   30  3607  3773:================================================
   32  2483  2846:================================================
   34  1756  2079:================================================
   36  1116  1394:================================================
   38   784   940:================================================
   40   559   508:================================================
   42   540   372:================================================
   44   448   227:================================================
   46   293   141:================================================
   48   263   111:================================================
   50   202    56:---------------------++++++++++++++++++++
   52   134    43:------------------++++++++++++++++++++++++
   54    99    30:-------------+++++++++++++++++++++++++++++++
   56    67    20:---------++++++++++++++++++++++
   58    55     9:-----++++++++++++++++++++++
   60    53    14:-------++++++++++++++++++
   62    37     9:-----+++++++++++++
   64    19     3:--++++++++
   66     9     0:+++++
   68    11     2:-+++++
   70     9     0:+++++
   72     3     3:==
   74     8     1:-+++
   76     5     2:-++
   78     5     0:+++
   80     1     0:+
  > 80    25     8:----+++++++++
```

Fig. 10

```
12411076 residues in 42215 sequences
mean initn score: 26.0 (7.30)
mean init1 score: 25.6 (6.51)
5864 scores better than 33 saved, ktup: 2, fact: 8    scan time: 0:02:29
The best scores are:                                  initn init1  opt
>A25660   Cytochrome P450 101 - Pseudomonas putida    2050  2050  2050
>O4PSCP   Cytochrome P450 101 - Pseudomonas putida    1999  1801  2003
>O4BS6M   Cytochrome P450 106 - Bacillus megaterium    257    99   364
>A40401   Cytochrome P450 55 precursor - Imperfect     214   132   282
>S18924   *Cytochrome P-450soy - Streptomyces grise    172   113   392
>A35401   Cytochrome P450 105A1 - Streptomyces gris    168   125   383
>B35401   Cytochrome P450 105B1 - Streptomyces gris    155    91   367
>S15809   *Cytochrome P450-like protein - Streptomy    143    90   325
>A27555   Steroid 21-monooxygenase cytochrome P450     111    76    78
>A24101   Steroid 21-monooxygenase cytochrome P450     111    74    76
```

| | | | | |
|---|---|---|---|---|
| >O4BOC2 | Steroid 21-monooxygenase cytochrome P450 | 111 | 76 | 78 |
| >A27865 | Steroid 21-monooxygenase cytochrome P450 | 111 | 71 | 80 |
| >A25446 | Steroid 21-monooxygenase cytochrome P450 | 111 | 71 | 80 |
| >O4HUC2 | Steroid 21-monooxygenase cytochrome P450 | 109 | 71 | 80 |
| >A32306 | Cytochrome P450 103 - Agrobacterium tumef | 109 | 58 | 248 |
| >A33813 | Cytochrome P450 27 precursor, mitochondri | 103 | 62 | 65 |
| >A26660 | Steroid 21-monooxygenase cytochrome P450 | 102 | 60 | 85 |
| >A32715 | Steroid 21-monooxygenase cytochrome P450 | 102 | 62 | 62 |
| >JQ1143 | Thromboxane-A synthase - Human #EC-number | 97 | 59 | 68 |
| >A39740 | *Sterol 27-hydroxylase precursor - Human | 90 | 55 | 57 |
| >MNHVRA | Nonstructural polyprotein - Ross River vi | 89 | 60 | 60 |
| >A29587 | Steroid 17alpha-monooxygenase cytochrome | 83 | 55 | 104 |
| >A40921 | *Steroid 17alpha-monooxygenase - Human #E | 83 | 55 | 104 |
| >A40908 | *Steroid 17alpha-monooxygenase (cytochrom | 83 | 55 | 104 |
| >A26366 | Steroid 17alpha-monooxygenase cytochrome | 83 | 55 | 104 |
| >S12969 | *Diacylglycerol kinase - Human #EC-number | 80 | 41 | 42 |
| >A26289 | Steroid 17alpha-monooxygenase cytochrome | 78 | 51 | 82 |
| >A39607 | *Mutation suppressor protein SRP3-1 - Yea | 78 | 35 | 45 |
| >S04346 | Steroid 17alpha-monooxygenase cytochrome | 78 | 51 | 89 |
| >GNVVTR | Genome polyprotein - Tomato ringspot viru | 77 | 45 | 46 |
| >QQBE47 | DNA-binding protein - Human herpesvirus 4 | 77 | 49 | 55 |
| >TDHULK | Leukocyte antigen-related protein precurs | 75 | 55 | 73 |

Fig. 12B

| | | | | |
|---|---|---|---|---|
| >B35342 | Steroid 11beta-monooxygenase 2 cytochrome | 75 | 50 | 81 |
| >S09736 | *Aldosterone synthase - Rat | 75 | 50 | 81 |
| >A32693 | *Steroid receptor protein svp 1 - Fruit f | 75 | 42 | 51 |
| >A35342 | Steroid 11beta-monooxygenase 1 cytochrome | 75 | 50 | 81 |
| >MNWVS | Nonstructural polyprotein - Sindbis virus | 74 | 64 | 64 |
| >VCLJG4 | env polyprotein - Simian immunodeficiency | 74 | 41 | 41 |
| >GNNYBT | Genome polyprotein - Coxsackievirus B3 | 73 | 59 | 59 |
| >GNNYB3 | Genome polyprotein - Coxsackievirus B3 | 73 | 59 | 59 |
| >S09156 | Diacylglycerol kinase, lymphyocyte - Pig | 73 | 35 | 36 |
| >A35867 | Cytochrome P450 71 - Avocado | 73 | 43 | 49 |
| >A41039 | *RNA-directed RNA polymerase - Rabbit hem | 73 | 41 | 51 |
| >A27124 | H+-transporting ATPase - Leishmania donov | 73 | 41 | 52 |
| >A32525 | Steroid 21-monooxygenase cytochrome P450 | 72 | 60 | 84 |
| >MNWV82 | Nonstructural polyprotein - Ockelbo virus | 71 | 61 | 61 |
| >DJBE28 | DNA-directed DNA polymerase - Human herpe | 71 | 41 | 41 |
| >JX0050 | Steroid 11beta-monooxygenase 3 cytochrome | 69 | 41 | 41 |
| >JX0071 | Steroid 11beta-monooxygenase (clone 7-1) | 69 | 41 | 41 |
| >A38819 | *Steroid 11beta-monooxygenase 2 (cytochro | 69 | 41 | 41 |
| >B26366 | Steroid 17alpha-monooxygenase cytochrome | 69 | 51 | 77 |
| >JX0151 | Steroid 11beta-monooxygenase 3 (cytochrom | 69 | 41 | 41 |
| >A28415 | Steroid 11beta-monooxygenase cytochrome P | 69 | 41 | 41 |
| >S15805 | *Cytochrome P450(11beta) - Bovine | 69 | 41 | 41 |

Fig. 12C

| | | | | |
|---|---|---|---|---|
| >KIECG | GTP pyrophosphokinase - Escherichia coli | 69 | 53 | 60 |
| >A29943 | Toll protein precursor - Fruit fly (Droso | 69 | 43 | 48 |
| >NCEC7 | Exodeoxyribonuclease VII large chain - Es | 68 | 57 | 66 |
| >C32575 | *C-ski protein FB27 - Chicken | 68 | 53 | 53 |
| >B41378 | *Cytochrome c553i precursor - Paracoccus | 68 | 68 | 79 |
| >TVFVSK | Transforming protein (ski) - Avian erythr | 68 | 53 | 53 |
| >S18188 | *Rat notch protein - Rat | 68 | 43 | 43 |
| >A40043 | *Notch protein homolog TAN-1 precursor - | 68 | 43 | 43 |
| >A32575 | *C-ski protein FB29 - Chicken | 68 | 53 | 53 |
| >A22363 | Cytochrome P450, phenobarbital-inducible | 68 | 46 | 51 |
| >S16873 | Cytochrome P450 2D4 - Rat | 67 | 39 | 87 |
| >A40457 | *Replication protein A 70K chain - Human | 67 | 67 | 76 |
| >B37222 | Cytochrome P450 1A2, hepatic - Dog (fragm | 67 | 57 | 91 |
| >S15435 | *Collagen alpha 1(VIII) chain - Human | 66 | 50 | 58 |
| >A39129 | *Catalase HPII - Escherichia coli IEC-num | 66 | 55 | 58 |
| >A34246 | Collagen alpha 1(VIII) chain precursor - | 66 | 50 | 62 |
| >S05962 | Radial spoke protein 3 - Chlamydomonas re | 65 | 39 | 39 |
| >S13178 | *6-Methylsalicylate decarboxylase - Penic | 65 | 41 | 46 |
| >A40440 | *Endothelin 1 and 2 receptor precursor, v | 65 | 43 | 45 |
| >A25076 | Tubulin alpha-1 chain - Yeast (Saccharomy | 65 | 39 | 40 |
| >S15074 | *Calpastatin - Rat | 65 | 50 | 51 |
| >A31270 | *Radial spoke protein 3 - Chlamydomonas r | 65 | 39 | 39 |

```
    HIV___ ✻ ___SW___5. 2. 1

HIV_FASTA1_SW_5. 2. 1
   HIV_FASTA1_SW_5. 5. 1
   HIV_FASTAN_SW_5. 2. 1
   HIV_FASTAN_SW_5. 5. 1
   HIV_FASTA0_SW_5. 2. 1
   HIV_FASTA0_SW_5. 5. 1
   HIV_SM-WT _SW_5. 2. 2
   HIV_SM-WT _SW_5. 5. 1
```

Fig. 13

```
TARGET:HIV
 SAME
  ┌─────────────┐ ┌─────────────┐ ┌─────────────┐
  │ FASTA1      │ │ FASTAN      │ │ FASTA0      │
  │ 5. 2. 1     │ │ 5. 2. 1     │ │ 5. 2. 1     │
  │   SW        │ │   SW        │ │   SW        │
  │             │ │             │ │             │
  │ LOCUS    1  │ │ LOCUS    1  │ │ LOCUS    1  │
  │ LOCUS    2  │ │ LOCUS    2  │ │ LOCUS    2  │
  │ LOCUS    3  │ │ LOCUS    4  │ │ LOCUS    3  │
  │ LOCUS    4  │ │ LOCUS    7  │ │ LOCUS    5  │
  │ LOCUS    5  │ │ LOCUS    3  │ │ LOCUS    7  │
  │ LOCUS    6  │ │ LOCUS    5  │ │ LOCUS    8  │
  └─────────────┘ └─────────────┘ └─────────────┘
        └2 1           └2 2           └2 3
```

Fig. 14

```
TARGET:HIV
      DIFF
┌─────────────┐  ┌─────────────┐  ┌─────────────┐
│ FASTA1      │  │ FASTAN      │  │ FASTA0      │
│ 5. 2. 1     │  │ 5. 2. 1     │  │ 5. 2. 1     │
│   SW        │  │   SW        │  │   SW        │
│             │  │             │  │             │
│ LOCUS  1    │  │ LOCUS  1    │  │ LOCUS  1    │
│ LOCUS  2    │  │ LOCUS  2    │  │ LOCUS  2    │
│ LOCUS  3    │  │ LOCUS  4    │  │ LOCUS  3    │
│ LOCUS  4    │  │ LOCUS  7    │  │ LOCUS  5    │
│ LOCUS  5    │  │ LOCUS  3    │  │ LOCUS  7    │
│ LOCUS  6    │  │ LOCUS  5    │  │ LOCUS  8    │
└─────────────┘  └─────────────┘  └─────────────┘
      └21              └22              └23
```

Fig. 17

```
TARGET:HIV
     DIFF
┌─────────────┐  ┌─────────────┐  ┌─────────────┐
│ FASTA1      │  │ FASTAN      │  │ FASTA0      │
│ 5. 2. 1     │  │ 5. 2. 1     │  │ 5. 2. 1     │
│   SW        │  │   SW        │  │   SW        │
│             │  │             │  │             │
│ LOCUS  1    │  │ LOCUS  1    │  │ LOCUS  1    │
│ LOCUS  2    │  │ LOCUS  2    │  │ LOCUS  2    │
│ LOCUS  3    │  │ LOCUS  4    │  │ LOCUS  3    │
│ LOCUS  4    │  │ LOCUS  7    │  │ LOCUS  5    │
│ LOCUS  5    │  │ LOCUS  3    │  │ LOCUS  7    │
│ LOCUS  6    │  │ LOCUS  5    │  │ LOCUS  8    │
└─────────────┘  └─────────────┘  └─────────────┘
      21              22                23
```

Fig. 20

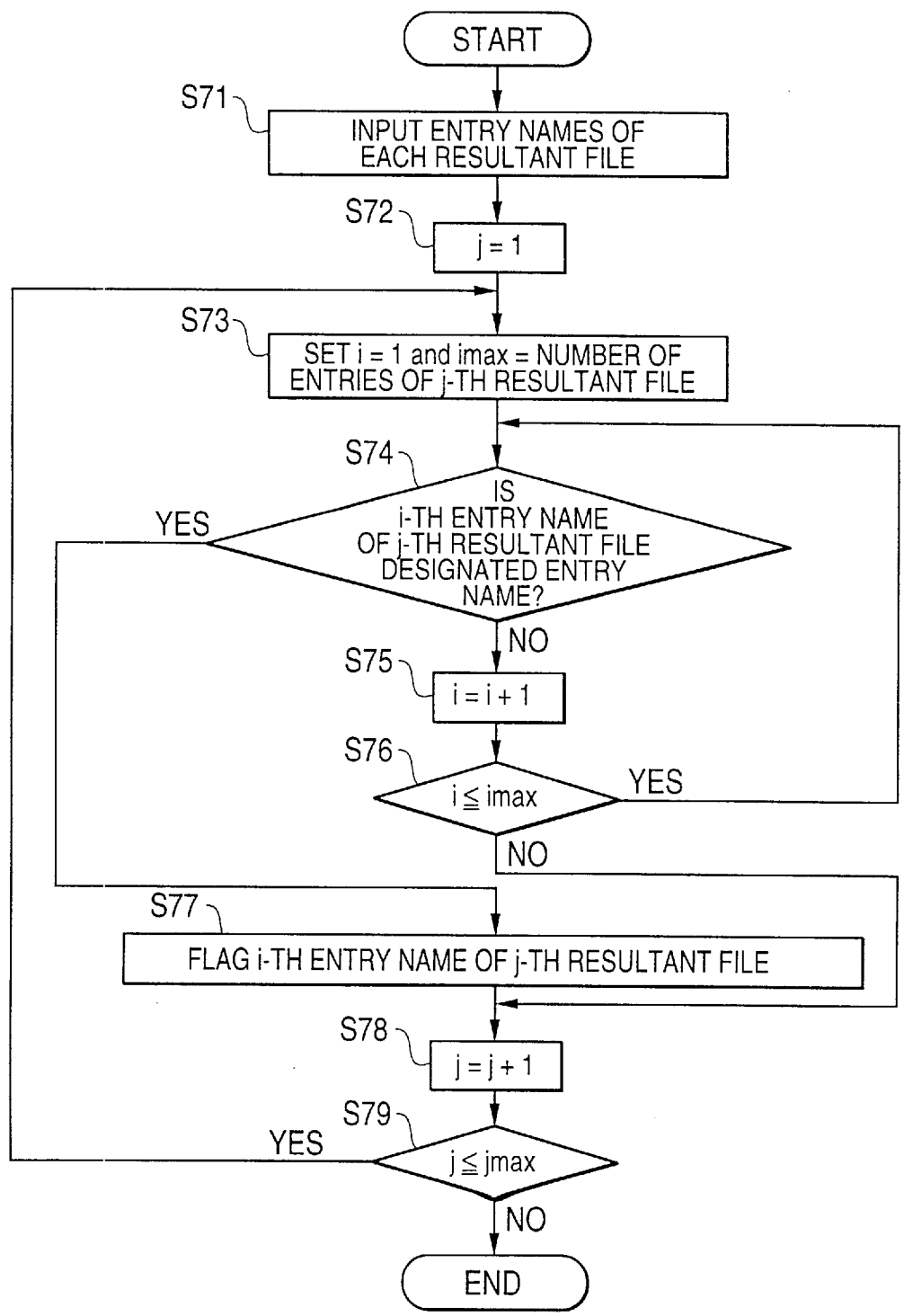

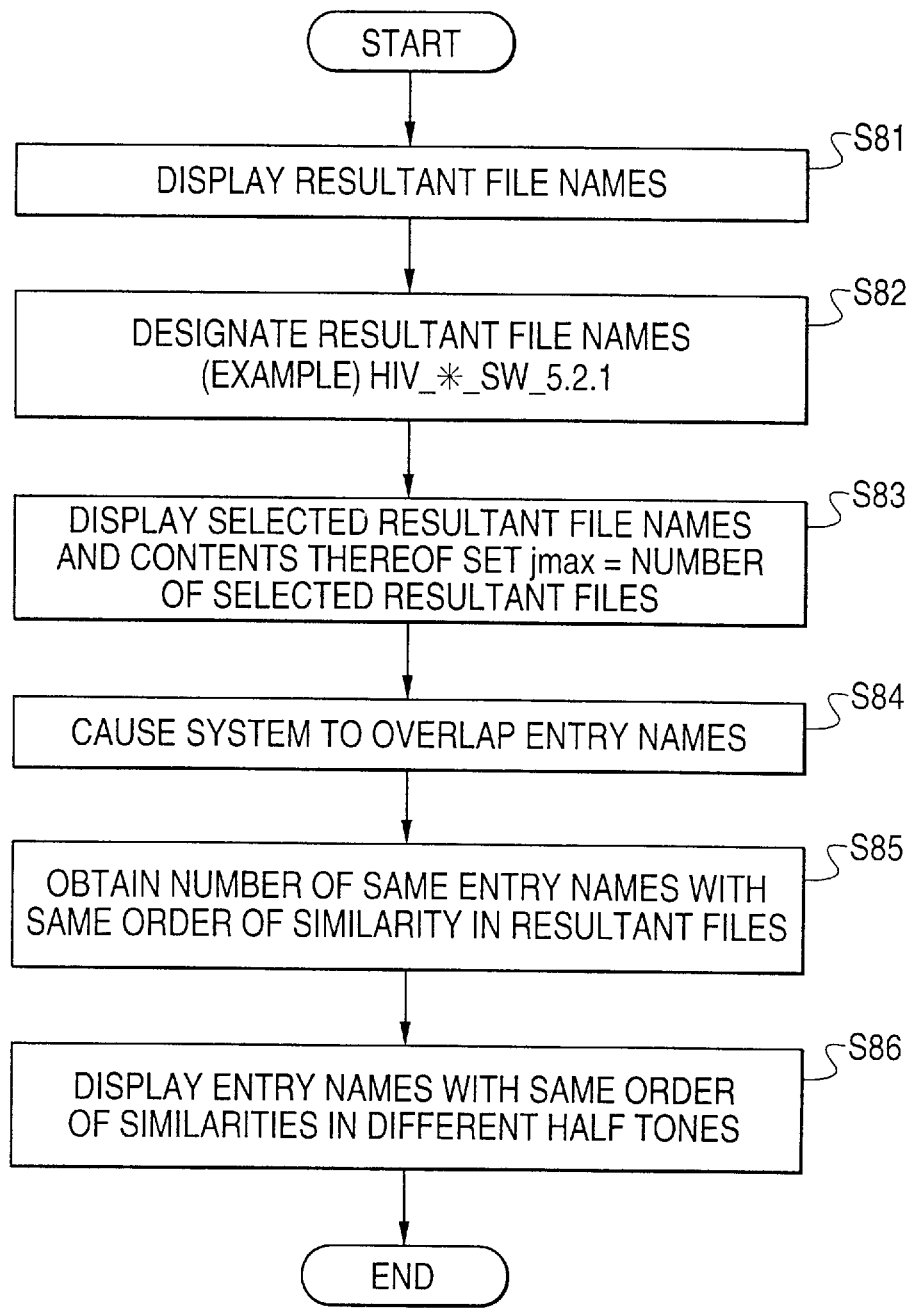

LIST PROCESS SYSTEM FOR MANAGING AND PROCESSING LISTS OF DATA

This application is a continuation of application Ser. No. 08/439,280, filed May 11, 1995, now abandoned.

BACKGROUND OF THE INVENTION

1. Field of the Invention

The present invention relates to a list process system and a method for processing a plurality of lists, each of which is composed of a plurality of data, and for extracting features thereof.

2. Description of the Related Art

Recent advancements in biotechnologies strongly influence our society, day by day. In particular, genetic engineering that involves gene recombinations of deoxyribonucleic acid (DNA), of which genes are composed, and protein engineering that synthesizes new proteins from existing proteins, have advanced remarkably.

DNA is a high molecular compound made up of nucleotide repeating units composed of a base, sugar (deoxyribose), and phosphoric acid. The bases that compose DNA are categorized in four types, namely: adenine (A), thymine (T), cytosine (C), and guanine (G). Between the nucleotides, the deoxyribose and phosphoric acid are linked in a double-stranded helix structure.

The bases are linked according to rules. Specifically, A and T are linked. In addition, C and G are linked. The sequence of these bases in DNA determines the type thereof (namely, the type of genes).

Since the sequence of bases of DNA records genetic information, in genetic engineering, a technique for exactly and quickly decoding a given complicated sequence of bases of DNA (gene sequences) is required.

A protein is a high molecular compound in which a lot of different amino acids are concatenated in a chain by peptide linkages. Polypeptide composed of only amino acids is called a simple protein. A compound of amino acids, nucleic acids, carbohydrate, phosphoric acid, and so forth is called a conjugated protein. A variety of functions of proteins depend on the sequence of amino acids that form polypeptide linkages, geometric disposition of the polypeptide chain, or the like. Thus, in protein engineering, a technique for exactly and quickly analyzing a sequence of amino acids of a given protein is required.

To determine the characteristics of a given gene and a given protein, the sequences are compared with all available sequences stored in databases. So the homologous sequences with the genetic sequence and so forth is obtained. In the methods for sequence databases search, similar regions are searched from the beginning of two sequences to be compared. In addition, the similarities of each region are calculated so as to evaluate the entire similarities of the sequence.

However, the method for the sequence database search has not been established. At the present time, various techniques are used in combination and the results are compared. In addition, there are many sequence databases that are used for the search. Thus, the results of the search for the same sequence data vary depending on the used method, database, parameters, and so forth.

Conventionally, the search is repeatedly performed with a combination of several methods, parameters, and so forth. By comparing the results, retrieved sequences are discarded or selected so that the most suitable searching method and parameters are obtained.

The results of the search are individually output in a list format and the similarities and differences thereof are manually determined.

In the conventional searching method, when the results of the search are few in number, they can be manually processed. However, as the number of results increases, the processing time becomes long and errors increase.

Devices that automatically read sequences of genes and amino acids have been widely used. In addition, as a result of big projects, such as the human genome project, that have been performed for decoding gene information, the amount of sequence data has increased remarkably. Thus, the amount of data of individually searching reaches the level that cannot be manually processed.

SUMMARY OF THE INVENTION

An object of the present invention is to provide a list process system and a method for effectively processing a plurality of lists, each of which is composed of plurality of data, and extracting the features thereof.

More specifically, the object of the present invention is to provide a list process system and a method for categorizing results of sequence database search in the fields of biotechnologies and so forth, so as to clarify features of similarities, differences, and so forth, of the results.

The present invention is a list process system and a method for use with an information process apparatus that processes data stored in databases.

A list process system according to the present invention comprises a list storing unit, a feature extracting unit, and a feature displaying unit. The list storing unit stores a plurality of lists, composed of a plurality of data, as results searched from a database. The feature extracting unit extracts features such as similarities and differences among the lists and outputs these features. The feature displaying unit displays the obtained features on a display screen or the like. Thus, the user can quickly grasp the features of the lists.

In addition, the list storing unit stores each list, adding order to the data that composes the list. Further, the list storing unit stores each list, adding information such as a method for search of a database to a file name of the list. The feature displaying unit displays the file names along with the features of the lists. Thus, the added information can be easily distinguished from the file names. A file with particular information can be easily selected from the displayed file names.

The feature displaying unit has for example a window function and a graphic function so that the user can clearly recognize the features of the lists. In addition, when the user designates some of lists displayed on the feature displaying unit, it can display the contents of the lists and the features thereof.

According to the list process system, even if the number of lists to be analyzed is huge or even if the amount of data included in one list is large, two lists can be quickly and automatically compared with each other.

For example, in the sequence database search that searches similar sequence of given sequence from a database, information of the type of a database, the type of a searching method, parameters, and so forth, is added to the file name of each list. The user can easily know these conditions that differ in lists from the file names. Thus, the user can compare a plurality of lists in a short time and obtain alternatives of similar data.

These and other objects, features and advantages of the present invention will become more apparent in light of the

BRIEF DESCRIPTION OF THE DRAWINGS

FIG. 2 is a table showing items that affect the results of sequence database search;

FIG. 5 is a table showing resultant file names according to the embodiment of the present invention;

FIG. 6 is a table showing a data structure of a resultant file according to the embodiment of the present invention;

FIG. 7 is an example of a score table used for homology retrieval;

FIG. 8 is a table showing sequence data being searched;

FIG. 9 is a table showing an example of a resultant file corresponding to FASTA;

FIGS. 10, 11 and 12A, 12B, and 12C show an example of a resultant file according to FASTA;

FIG. 13 is a schematic diagram showing a screen display for resultant file names according to the embodiment of the present invention;

FIG. 14 is a schematic diagram showing a screen display for common sequence names according to the embodiment of the present invention;

FIG. 17 is a schematic diagram showing a screen display for sequence names included in a designated resultant file according to the embodiment of the present invention;

FIG. 20 is a schematic diagram showing a screen display for sequence names that are not commonly included according to the embodiment of the present invention;

FIG. 25 is a flow chart showing an extracting process for designated sequence names according to the embodiment of the present invention;

FIG. 27 is a flow chart showing a displaying process for common sequence names each in the same order according to the embodiment of the present invention;

DESCRIPTION OF THE PREFERRED EMBODIMENT

Next, with reference to the accompanying drawings, an embodiment of the present invention will be described in detail.

Figure 1:
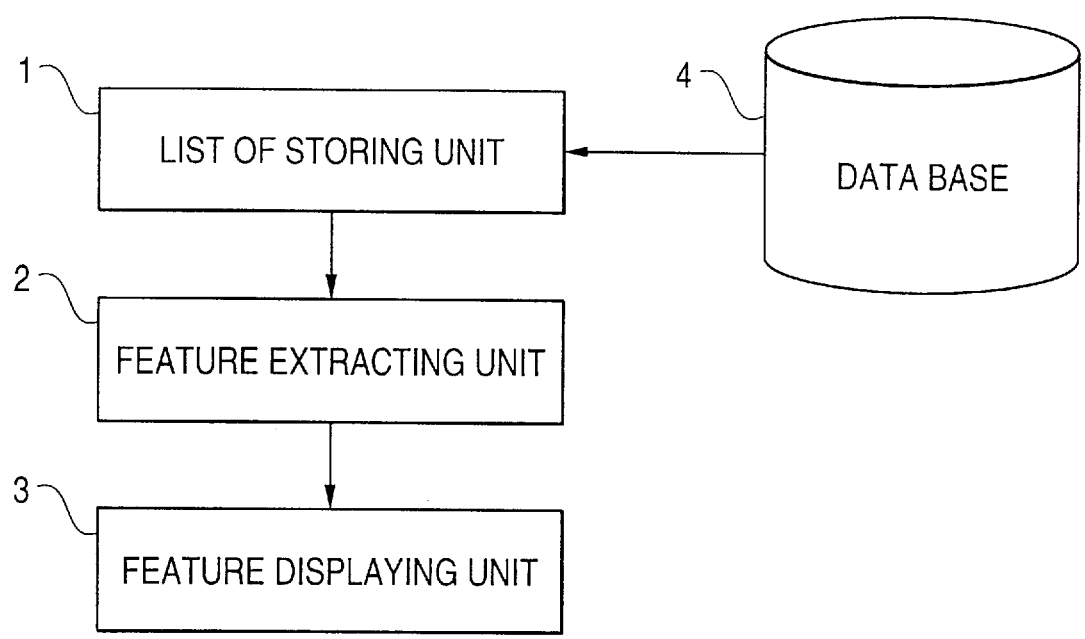
FIG. 1 is a schematic diagram showing a theoretical construction of an embodiment of the present invention.

FIG. 1 is a schematic diagram showing a theoretical construction of a list process system according to the present invention. The list process system according to the present invention comprises a list storing unit 1, a feature extracting unit 2, and a feature displaying unit 3 and performs processes with data stored in a database 4.

The list storing unit 1 stores a plurality of lists, each of which is composed of a plurality of data stored as results searched from the database 4. In addition, the list storing unit 1 stores an obtained list with a file name to which information used for searching sequences is added.

The list storing unit 1 stores each list, adding order the data that composes the list. In addition, the list storing unit 1 stores each list, adding information, which has been used for adding order, to the file name of the list.

When the database 4 is a database used for sequence database search, the list storing unit 1 stores a plurality of lists in which order numbers are added to the identifiers of data similar to given data. In addition, the list storing unit 1 adds to the file name information such as the identifier of the given data, the identifier of the technique used for adding order numbers to the identifiers of similar data, the identifier of the database 4, or parameters for the method, and stores the resultant file so as to manage the lists.

The feature extracting unit 2 extracts features such as similarities and differences between the lists stored in the list storing unit 1.

The feature displaying unit 3 has a window function and a graphic function. The feature displaying unit 3 displays the file names of the lists on a screen at a time. When the user designates several file names, the feature displaying unit 3 displays the contents of the lists having the designated file names. In addition, the feature displaying unit 3 displays the features that are output from the feature extracting unit 2 on the screen using the window function or the graphic function.

Figure 3:
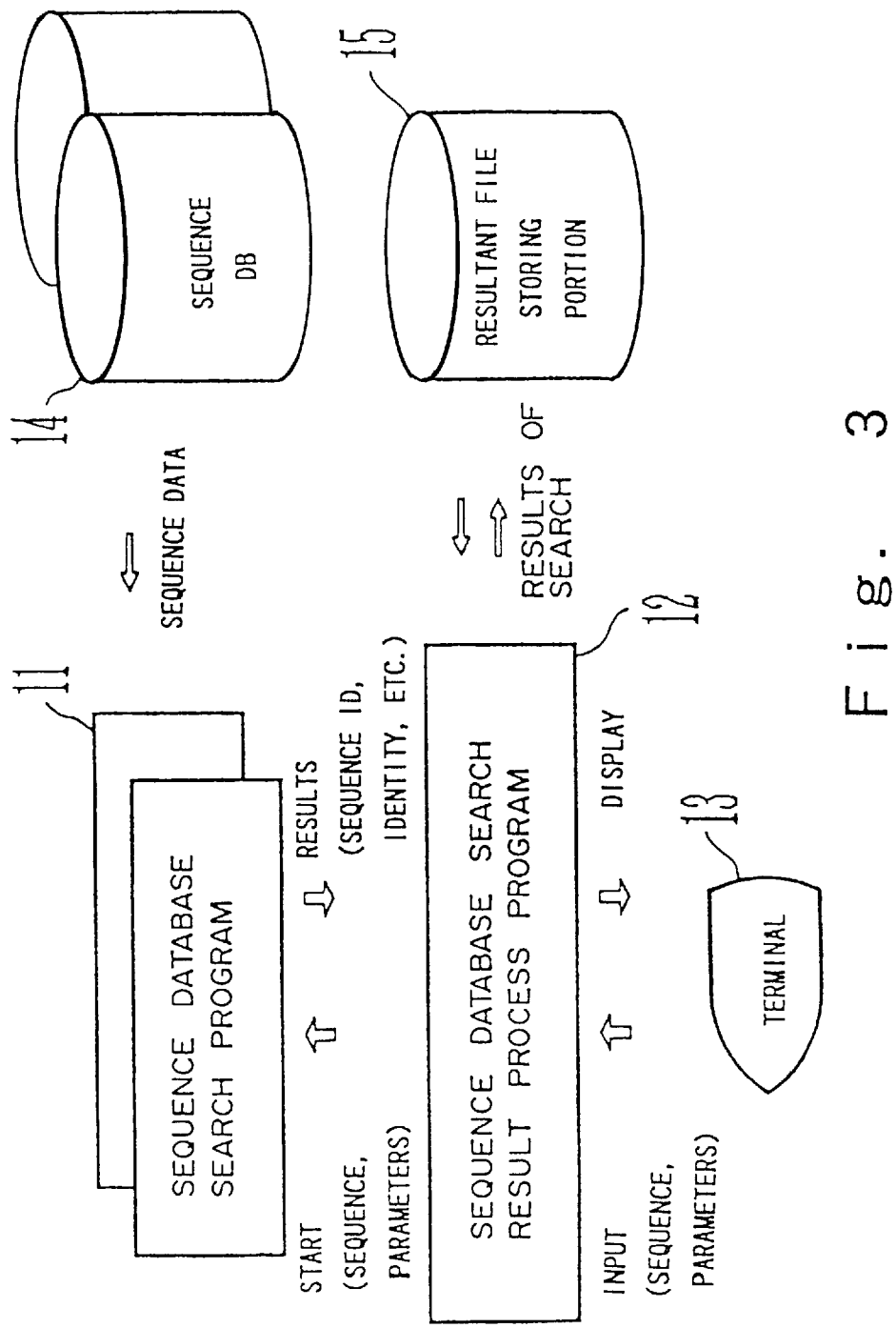
FIG. 3 is a schematic diagram showing a construction of the embodiment of the present invention.

For example, the list storing unit 1 of the present invention is a resultant file storing portion 15 shown in FIG. 3. The feature extracting unit 2 is a processor that executes a sequence database search result process program 12. The feature displaying unit 3 comprises a processor for executing the sequence database search result process program 12 and a terminal 13.

The list storing unit 1 adds information such as data and the identifier of the method to the file name of the list. The feature displaying unit 3 displays the resultant file name on the screen. Thus, the user can know at a glance how each list is obtained. In addition, the user can easily select a list having particular information from the displayed lists having file names.

For example, when a sequence name, a name of method for sequence database search, and so forth are added as a file name to the list of sequence names of sequence data obtained from the search, the user can know what searched results are stored in the file without needing to see the content of the list (file).

In addition, the feature extracting unit 2 extracts the features such as similarities and differences between the lists. Moreover, the feature extracting unit 3 clearly displays the extracted features on the screen. Thus, the user can effectively know which features exist between the lists. When the results of the search are processed, it is not necessary to manually compare searched sequence names. Even if the number of sequence names included in the retrieved results is huge or even if many lists of retrieved results are compared, the lists can be processed at high speed. When the extracted features are graphically displayed with the graphic function, the user can more clearly know the features.

Next, an embodiment of the present invention applied to the field of biotechnologies will be described.

FIG. 2 is a table showing a plurality of items that affect the results of the sequence database search in the field of biotechnologies. In FIG. 2, item "sequence" is a sequence of bases of a gene to be searched or a sequence of amino acids of a protein to be searched.

FASTA, BLAST (Basic Local Alignment Search Tool), and Smith-Waterman method are known as the methods for sequence database search. In FASTA, two sequences of data to be compared are segmented by a unit length. By moving a unit to be compared, the similarities are calculated. Although BLAST is similar to FASTA, BLAST is a method for regarding partial similarities as more important than FASTA. In BLAST, results can be more quickly obtained than in FASTA. In Smith-Waterman, although exact results can be obtained, since a plurality of algorithms are used, it takes a long time to obtain the results.

As sequence databases, there are DDBJ (DNA Data Bank of Japan), GenBank (Genetic Sequence Data Bank) of the United States, nucleotide sequence database of EMBL (European Molecular Biology Laboratory), nucleic acid sequence databases of NBRF (National Biomedical Research Foundation), SWISS-PROT (Swiss Protein Sequence Data Bank), and so forth.

In FIG. 2, the item "parameter" is a parameter that is used in each method for sequence database search. The results depend on parameters used even if the same method is used.

Since all users require their results, the results should be displayed when necessary. Thus, a system that can easily read data from a resultant file group corresponding to a designated file name is required.

FIG. 3 is a schematic diagram showing a construction of a sequence database search result process system according to the embodiment of the present invention. The system shown in FIG. 3 comprises a sequence database (sequence DB) 14, a resultant file storing portion 15, a terminal 13, a program memory (not shown), and a processor (not shown). The sequence database 14 stores known sequence data. The resultant file storing portion 15 stores lists of sequence data obtained as results of sequence database search. The terminal 13 is used to input and output data. The program memory stores programs. The processor executes the programs. The sequence database search program 11 and the sequence database search result process program 12 are stored in the program memory and executed by the processor.

In the sequence database search, a homologous sequence of a given sequence is searched from the sequence database 14. The results are output in order of higher homology. The index of the sequence database search depends on the method to be used. Generally, the homology is represented by an index called identity.

The sequence database search program 11 is composed of a plurality of searching programs corresponding to a plurality of algorithms for sequence database search. The sequence database search program 11 is called from the sequence database search result process program 12. The sequence database 14 represents one of a plurality of databases.

A sequence to be searched is input by a variety of methods such as keyboard input from the terminal 13 by the user, sequence database, and sequencer (sequence reading device). When a method for sequence database, parameters thereof, and a database to be searched are designated and input from the terminal 13, the sequence database search result process program 12 sends the received information to the designated sequence database search program 11 so as to cause the sequence database search program 11 to perform sequence database search in the designated sequence database 14. The results are sent to the sequence database search result process program 12. The results are, for example, an identifier of sequence data retrieved (sequence ID) and a value of identity.

The sequence database search result process program 12 temporarily stores the results in the resultant file storing portion 15 and causes the sequence database search program 11 to retrieve the same sequence corresponding to the other designated method and parameters. By repeating this process, a plurality of resultant files oriented to the same sequence are obtained. Thereafter, the sequence database search result process program 12 extracts features such as similarities and differences of the resultant files and displays these features on the terminal 13. The features among the resultant files extracted can also be output using a printer or the like (not shown).

Figure 4:
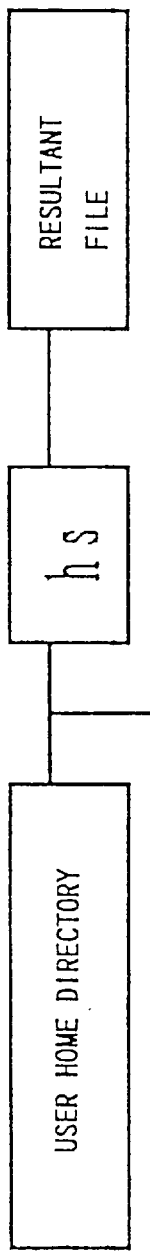
FIG. 4 is a schematic diagram showing a naming rule of a resultant file according to the embodiment of the present invention.

As a precondition, the system of the embodiment operates in a UNIX environment. Each file is created in the directory structure of UNIX. As shown in FIG. 4, the resultant files are created in a dedicated directory hs for this system under the user's home directory.

As shown in FIG. 4, the file name of the resultant file is delimitated by each category item in FIG. 2. Thus, the file name is composed of identifiers for sequence name, name of method, and database (DB) name and parameters. For example, in the file name HIV11_FASTA_SW_5.5.1 shown in FIG. 4, HIV11 represents an unknown sequence name to be searched. FASTA represents a name of method used for search. SW (SWISS-PROT) represents the name of a database to be used for the search. 5.5.1 represents parameters used for FASTA. Thus, when the file name is controlled corresponding to such a naming rule, the technique, database, and parameters used for each sequence can be recognized at a glance from the file name.

FIG. 5 is a table showing resultant file names created under the directory hs. HIV (Human Immunodeficiency Virus), LYSO (Lysozyme), UBIQ (Ubiquitin), LECTIN, and TRYPSIN represent sequence names to be retrieved. FASTA1, FASTAN, and FASTA0 represent three different types of FASTA. SM-WT represents Smith-Waterman method. SW represents the database SWISS-PROT. 5.2.1 and so forth represent parameters used for respective method for sequence database search.

FIG. 6 shows an example of data structure of each resultant file. The resultant file shown in FIG. 6 is mainly composed of detail contents of information described in the file name and information with respect to the searched sequence.

In the example shown in FIG. 6, parameters 5.2.1 denoted in the file name represent that gap penalty U=5, gap penalty V=2, and ktup=1. The ktup parameter determines how many consecutive identities are required to be compared at a time in FASTA. For example, in this example (ktup=1), FASTA examines only those portions of the two sequences being compared that have at least two adjacent identical residues in both sequences. The details of the gap penalty U and the gap penalty V will be described later.

In addition, it is clear that the real sequence name of the target is HIV-1 PROTEASE and that the database searched is SWISS-PROT.

LIST is a list of entry names of sequences searched from the database and their scores, in which the entry names are arranged in the descending order of scores. The entry names of the sequences are identifiers or identifying names of sequence data that depend on each database. In FIG. 6, as an entry name of SWISS-PROT, for example, HIV_MANMA and so forth are shown. The scores represent identity values of sequence data. If the score is larger, it has greater similarities to the sequence to be searched. For example, since the score of HIV_MANMA is 1133, it is clear that HIV_MANMA is most similar to HIV-1 PROTEASE.

FIG. 7 shows an example of a score table for protein sequence, used for score calculations with FASTA. The score table shown in FIG. 7 is a matrix that represents the similarities between two amino acids. The rows and columns of the matrix represent names of amino acids A to Z as components. X represents the name of an amino acid that cannot be specifically identified. The numerical value of the intersection of each row and each column represents the similarity of corresponding amino acids. As the numerical value becomes larger, the similarity increases. The numerical value is determined corresponding to the characteristics of amino acids. There are several types of score tables and one of them is selected depending on a sequence to be searched.

In FASTA, an amino acid in one of target protein sequence is searched for from the row of the score table. The corresponding amino acid of a sequence in the database is searched for from the column of the score table. The numerical value of the intersection is added to the score of the sequence data. After the additions for all the amino acids are finished, sequence data with scores that are greater than a predetermined threshold value are treated as similar protein sequences of the target sequence.

However, when pairs of sequences are successively compared, the scores of the sequence data do not always increase. Thus, a technique for placing a gap between two successive amino acids is used so as to improve similarities.

FIG. 8 shows examples of sequence obtained by FASTA. In FIG. 8, each alphabetic letter represents the name of an amino acid on the row of the matrix shown in FIG. 7. Symbol "-" represents a gap. In these sequence data, all amino acids at each position marked with a * mark accord with each other. When a sequence is searched without gaps, since there are amino acids G and S that are different from those in other sequences at the left end of a sequence A33813 at the third row from the bottom, the sequence A33813 deviates largely from other sequences. Thus, the score of the sequence A33813 becomes low. Consequently, although there are amino acids that accord with other sequences at a plurality of positions denoted by *, the sequence A33813 may not be obtained as a result of sequence database search.

By placing gaps, a sequence that has a possibility of being missed may be searched. However, if the user relies on this method too much, the scores will be too large and a sequence that does not have similarities may be searched. To prevent this problem, when gaps are placed, a penalty P that is calculated by the following equation is subtracted from the score, so as to suppress the increase of that score.

$$P = UL + V \tag{1}$$

In expression (1), U and V are gap penalties shown in FIG. 6. In this case, U=5 and V=2. L represents the length of a gap being placed (the number of structural units). As is clear from expression (1), the penalty P is represented by a linear function of L. The values of the gap penalties U and V are given as parameters of sequence database search along with ktup. Since the scores vary depending on the parameters to be used, the sequence to be searched also vary.

FIGS. 9 to 12 show an example of a resultant file of sequence database search obtained corresponding to FASTA for CYTOCHROME, which is one type of protein.

FIG. 9 shows file names searched from a database. FIG. 10 shows the number of sequences obtained as similar sequences along with a range of the score. In FIG. 10, numerical values in the leftmost column represent a range of the scores. Numerical values of the column initn represent the number of sequences having scores in the case that gaps are inserted. Numerical values of the column init1 represent the number of sequences with scores in the case that gaps are not inserted.

The graph on the right part of FIG. 10 shows the number of sequences in the cases of initn and init1. "=", "−", and "+" each represent two sequences. "−" represents sequences in the case of init1. "+" represents sequences that are increased due to gaps in the case of initn.

FIGS. 11 and 12A, 12B, and 12C show a list of names and scores of sequences of which scores of init1 exceed 33. The first row of FIG. 11 represents that 12411076 amino acids of 42215 sequences are compared. The second and third rows show mean values of scores in the case of initn and init1. The fourth row shows that the score of each of 5864 sequences exceeds 33.

The numerical values in the column initn show scores in the case gaps are inserted. The numerical values in the column init1 show scores in the case gaps are not inserted. The numerical values in the column opt show values of which the results in the case of init1 are aligned according to the known Needleman-Wunsh-Sellers alignment and scores are recalculated. In FIGS. 11 and 12A, 12B, and 12C sequence names are arranged in the descending order of scores of initn. The order of sequence names in a resultant file depends on the method for sequence database search and parameters thereof.

When many resultant files that are obtained with different methods for sequence database search and parameters are stored in the resultant file storing portion 15, the sequence database search result process program 12 causes the display of the terminal 13 to display the list of the obtained resultant file names.

FIG. 13 shows a screen displaying file names with respect to HIV of the resultant files shown in FIG. 5. In FIG. 13, the user can select a plurality of resultant files so that the sequence database search result process program 12 processes sequence data of the selected resultant files. The selecting operation is performed by inputting a particular name of method and database name from the terminal 13.

In FIG. 13, for example, sequence name HIV, database name SW, and parameters 5.2.1 are designated. However, a name of method is not designated but is a wild card *. Thus, three files HIV_FASTA1_SW_5.2.1, HIV_FASTAN_SW_5.2.1, and HIV_FASTA0_SW_5.2.1 are displayed in a half-tone. The sequence database search result process program 12 reads the selected resultant files from the resultant file storing portion 15, extracts features such as similarities and differences between the search results, and outputs these features to the terminal 13 or the like.

Next, with reference to FIGS. 14 to 31, examples of features of search results displayed on screens and extracting methods thereof will be described.

FIGS. 14, 17, 20, 23, 26, and 29 show screens that display examples of various features extracted for the three selected resultant files (FIG. 13). In these drawings, TARGET at the top of each screen represents a sequence name HIV to be searched. Display regions 21, 22, and 23 display entry names of sequence data included in resultant files HIV_FASTA1_SW_5.2.1, HIV_FASTAN_SW_5.2.1, and HIV_FASTA0_SW_5.2.1, respectively in the descending order of scores. In these examples, LOCUS 1 and so forth represent entry names equivalent to respective sequence data. At the upper portions of the display regions 21, 22, and 23, names of method, parameters, and database names of the resultant files are displayed.

FIGS. 15, 16, 18, 19, 21, 22, 24, 25, 27, 28, 30, and 31 are flow charts showing feature extracting processes performed by the sequence database search result process program 12.

FIG. 14 shows a screen that displays examples of sequences included in all selected resultant files. In FIG. 14, since entry names LOCUS 1, LOCUS 2, LOCUS 3, and LOCUS 5 are included in all the three resultant files, they are displayed in a half-tone as similarities among the resultant files.

Figure 15:
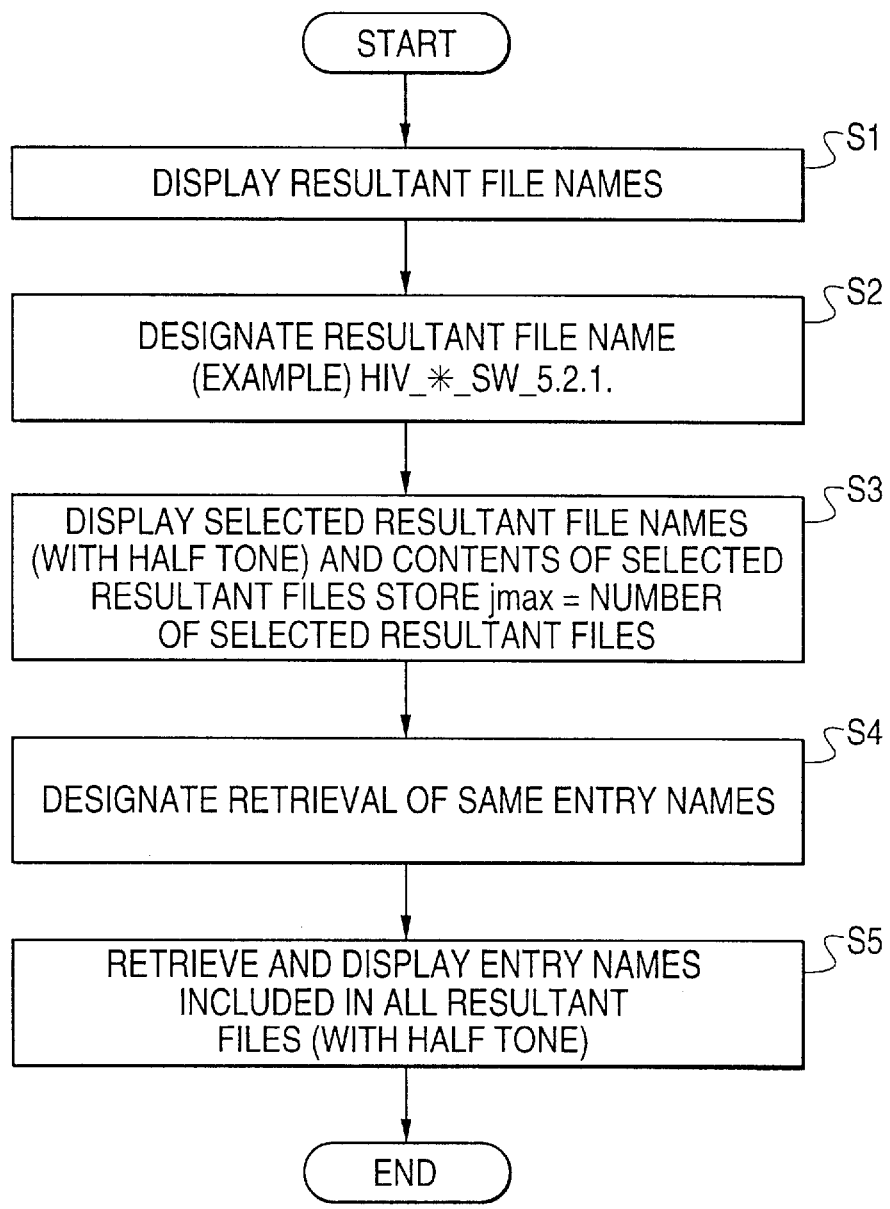
FIG. 15 is a flow chart showing a displaying process for common sequence names according to the embodiment of the present invention.

FIG. 15 is a flow chart showing a process for selecting resultant files and a process for extracting similarities shown in FIG. 14. In FIG. 15, when the process is started, a list of resultant files as shown in FIG. 13 is displayed (at step S1). When the user inputs information that designates resultant file names from the terminal 13 (at step S2), the resultant file names corresponding to the information are selected and displayed in a half-tone (at step S3). Thereafter, the contents of the selected resultant files are displayed as shown in FIG. 14. The number of the selected resultant files is stored as jmax in a memory (not shown). When the user causes the system to retrieve common entry names in the selected resultant files (at step S4), they are retrieved and displayed in a half-tone (at step S5).

Figure 16:
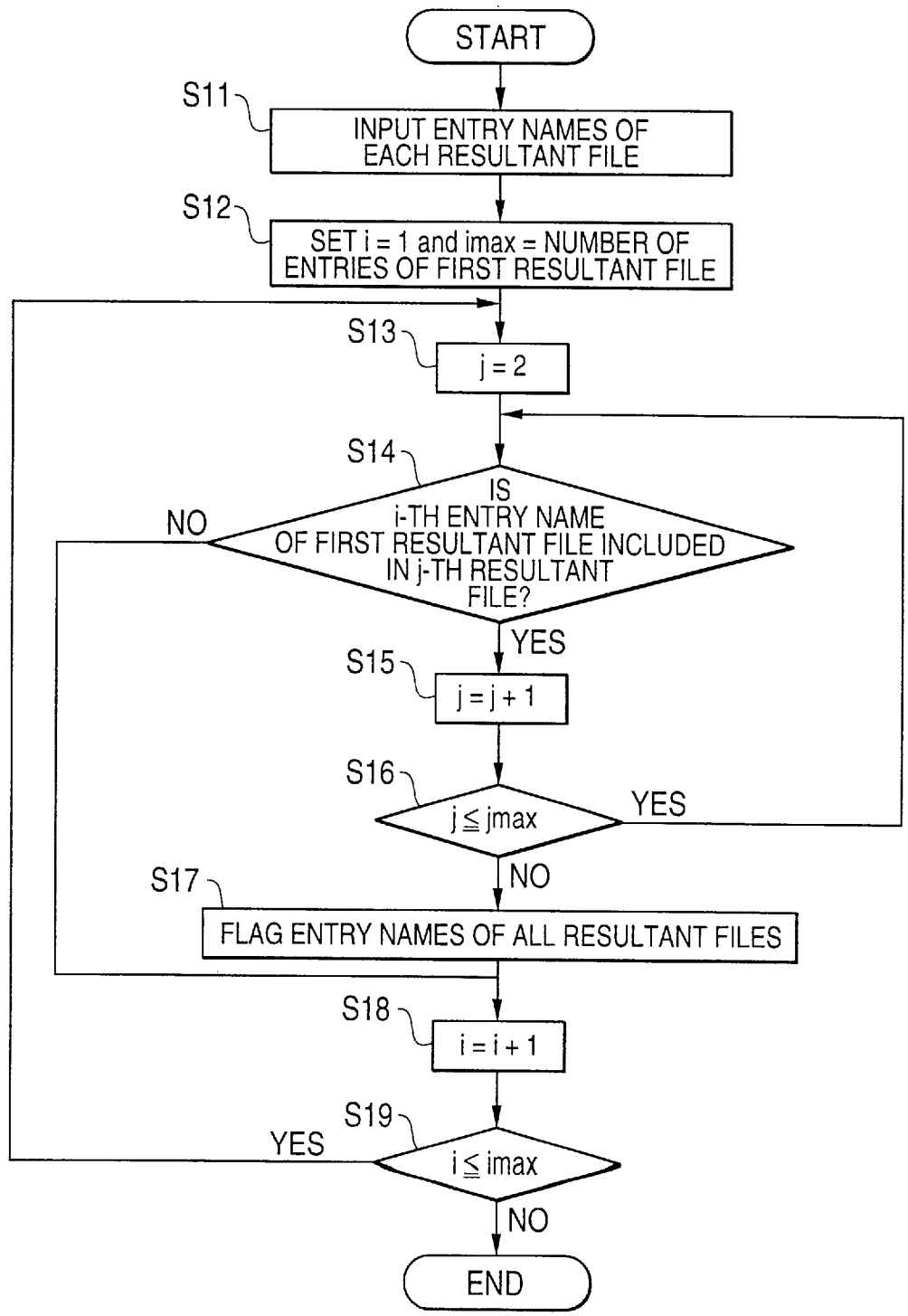
FIG. 16 is a flow chart showing an extracting process for common sequence names according to the embodiment of the present invention.

FIG. 16 is a flow chart showing the process at step S5 (FIG. 15) of the sequence database search result process program 12. The process shown in FIG. 16 is executed by a subroutine called from the process shown in FIG. 15 or by a different process from the process shown in FIG. 15. In FIG. 16, entry names of sequences of each resultant file are input to the subroutine or the different process (at step S11). i=1 is set and the number of entries of the first resultant file is set to imax (at step S12). For example, in FIG. 14, the content of the first resultant file is displayed in the display region 21. Thus, imax=6. The contents of the second and third resultant files are displayed in the display regions 22 and 23, respectively.

Thereafter, j=2 is set (at step S13). Next, it is determined whether or not the i-th entry name of the first resultant file is included in the j-th resultant file (at step S14). When the determined result is YES, j is incremented by "1" (j=j+1) (at step S15). Thereafter, the value of j is compared with the value of jmax (at step S16). When the value of j does not exceed the value of jmax at step S16 (the determined result at step S16 is YES), processing returns to step S14. From step S14, the same processes are repeated.

When the value of j exceeds the value of jmax at step S16 (the determined result at step S16 is NO), it is clear that the entry name is included in all the resultant files. At this point, the related entry names of all the resultant files are flagged (at step S17). Thereafter, i is incremented by "1" (i=i+1) (at step S18). Next, the value of i is compared with the value of imax (at step S19).

When the determined result at step S14 is NO, processing advances to step S18 (skipping steps S15 to S17).

When the value of i does not exceed the value of imax at step S19 (the determined result at step S19 is YES), processing returns to step S13. From step S13, the same processes are repeated. When the value of i exceeds the value of imax, the process is finished (the determined result at step S19 is NO). Thereafter, at step S5 shown in FIG. 15, the flagged entry names of each resultant file are displayed in a half-tone.

In the case as shown in FIG. 14, the process at step S17 is performed for the entry names LOCUS 1, LOCUS 2, LOCUS 3, and LOCUS 5 corresponding to i=1, 2, 3, and 5, respectively. In the display regions 21, 22, and 23, these entry names are displayed in a half-tone. For the entry names LOCUS 4 and LOCUS 6 corresponding to i=4 and 6, respectively, since the determined results at step S14 for j=3 and 2 are NO, the process at step S17 is not performed. Thus, the entry names LOCUS 4 and LOCUS 6 are not displayed in a half-tone.

FIG. 17 shows a screen that displays examples of sequences that are different from those in a designated resultant file. In FIG. 17, the user designates a resultant file from the display region 22. Since entry names LOCUS 6 and LOCUS 8 of other resultant files are not included in the designated resultant file, these entry names are displayed in a half-tone in the display regions 21 and 23 as differences from the designated resultant file.

Figure 18:
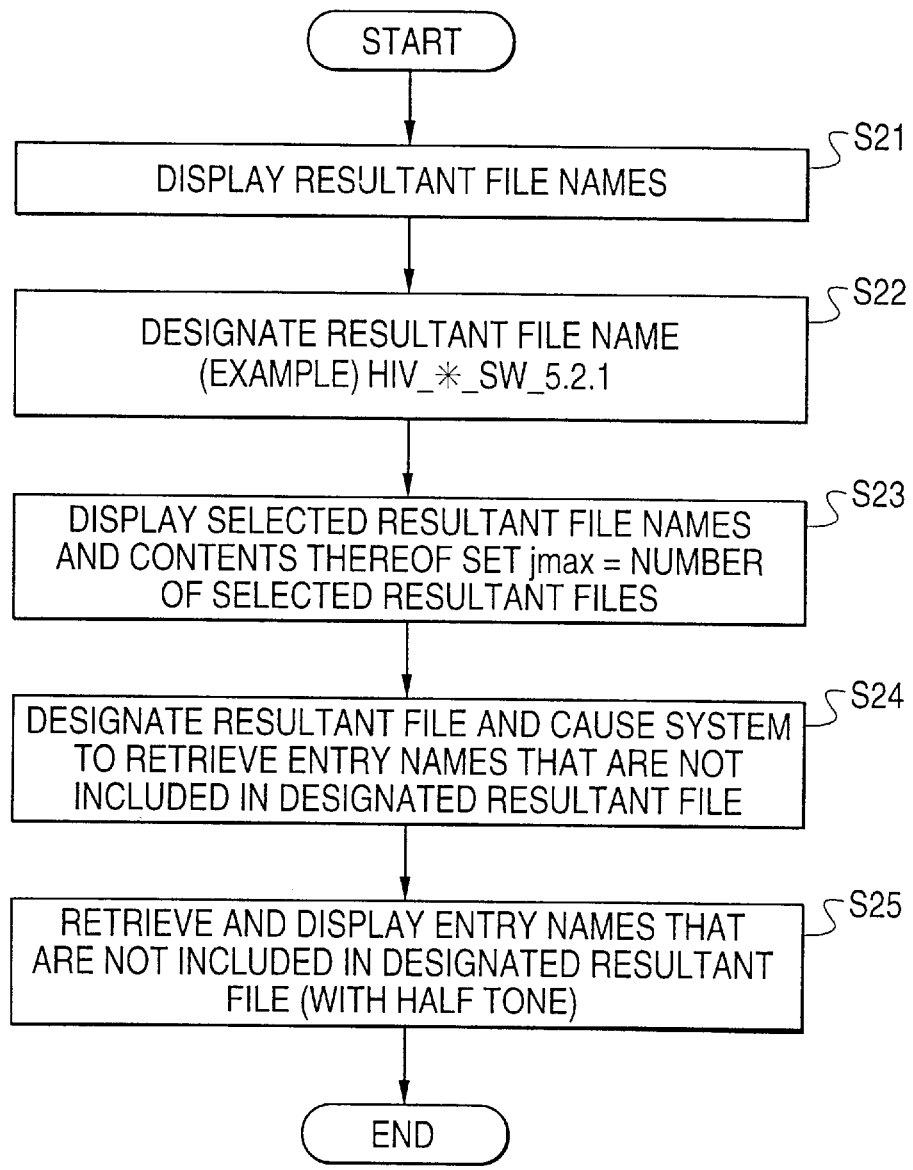
FIG. 18 is a flow chart showing a displaying process for sequence names that are not included in a designated resultant file according to the embodiment of the present invention.

FIG. 18 is a flow chart showing a process for selecting resultant files and a process for extracting differences as shown in FIG. 17. The processes at steps S21, S22, and S23 shown in FIG. 18 are the same as those at step S1, S2, and S3 shown in FIG. 15, respectively. After step S23, the user designates a resultant file and causes the system to retrieve entry names that are not included in the designated resultant file (at step S24). Thus, the required retrieving operation is performed and the results are displayed in a half-tone (at step S25).

Figure 19:
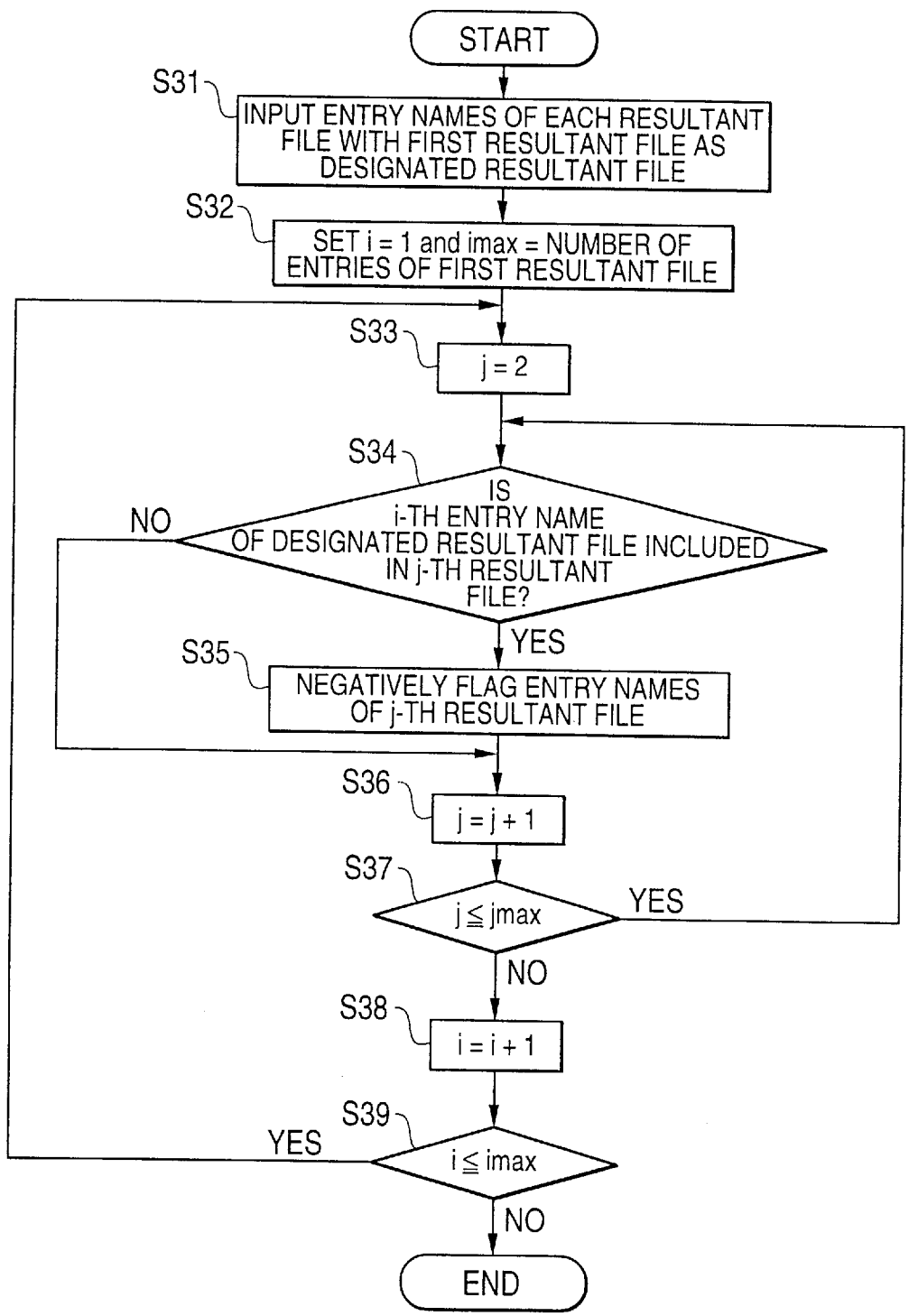
FIG. 19 is a flow chart showing an extracting process for sequence names that are not included in a designated resultant file according to the embodiment of the present invention.

FIG. 19 is a flow chart showing the process at step S25 (FIG. 17) of the sequence database search result process program 12. In FIG. 19, entry names of sequences of each resultant file are input to a subroutine or the like with the first resultant file as the designated resultant file (at step S31). i=1 is set and the number of entries of the first resultant file is set to imax (at step S32). In FIG. 17, the content of the first resultant file is displayed in the display region 22. Thus, imax=6. The contents of the second and third resultant files are displayed in the display regions 21 and 23, respectively.

Thereafter, j=2 is set (at step S33). It is determined whether the i-th entry name of the designated (first) resultant file is included in the j-th resultant file (at step S34). When the determined result is YES, entry names of the j-th resultant file are negatively flagged (at step S35). j is incremented by "1" (at step S36). Thereafter, the value of j is compared with the value of jmax (at step S37). When the determined result at step S34 is NO, processing advances to step S36 (skipping step S35).

When the value of j does not exceed the value of jmax at step S37 (the determined result at step S37 is YES), processing returns to step S34. From step S34, the same processes are repeated.

When the value of j exceeds the value of jmax at step S37 (the determined result at step S37 is NO), i is incremented by "1" (at step S38). Thereafter, the value of i is compared with the value of imax (at step S39).

When the value of i does not exceed the value of imax at step S39 (the determined result at step S39 is YES), processing returns to step S33. From step S33, the same processes are repeated. When the value of i exceeds the value of imax, the process is finished (the determined result at step S39 is NO). Thereafter, at step S25 shown in FIG. 18, entry names that are not negatively flagged (those of the non-designated resultant files) are displayed in a half-tone.

In FIG. 17, the process at step S35 is performed for entry names LOCUS 1, LOCUS 2, LOCUS 4, LOCUS 7, LOCUS 3, and LOCUS 5 included in the designated resultant file of the display region 22. The entry names in the display regions 21 and 23 are not displayed in a half-tone. On the other hand, since the process at step S35 is not performed for LOCUS 6 in the display region 21 and LOCUS 8 in the display region 23, these entry names are displayed in a half-tone.

FIG. 20 shows a screen that displays examples of sequences that are not included in all of the selected resultant files. As shown in FIG. 14, entry names of sequences included in all the selected resultant files are LOCUS 1, LOCUS 2, LOCUS 3, and LOCUS 5. In FIG. 20, the other entry names LOCUS 4, LOCUS 6, LOCUS 7, and LOCUS 8 are displayed in a half-tone as differences between the resultant files in the display regions.

Figure 21:
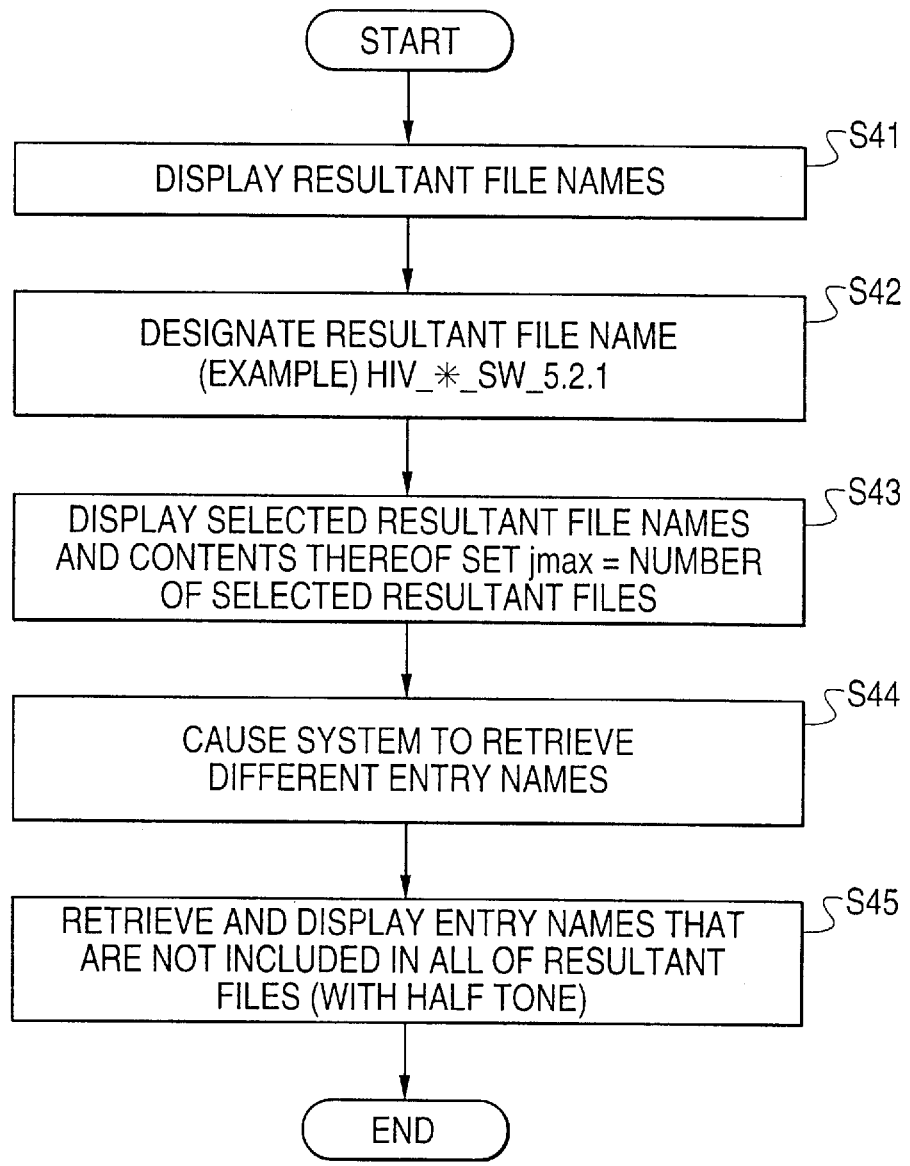
FIG. 21 is a flow chart showing a displaying process for sequence names that are not commonly included according to the embodiment of the present invention.

FIG. 21 is a flow chart showing a process for selecting resultant files and a process for extracting differences as shown in FIG. 20. The processes at steps S41, S42, and S43 shown in FIG. 21 are the same as the processes at steps S1, S2, and S3 shown in FIG. 15, respectively. After step S43, when the user causes the system to retrieve sequences that are not included in all of the designated resultant files (at step S44), the required retrieving operation is performed and the results are displayed in a half-tone (at step S45).

Figure 22:
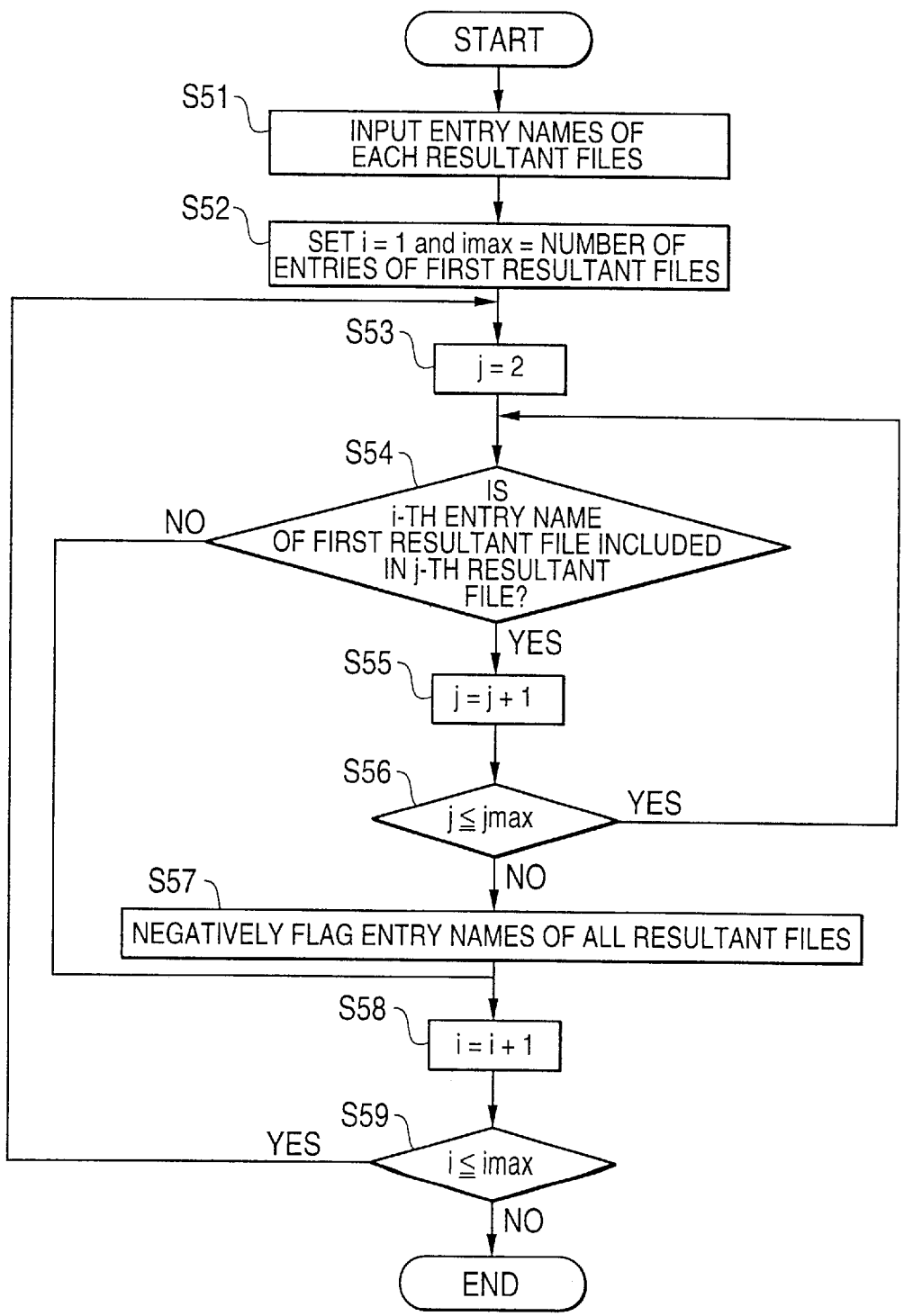
FIG. 22 is a flow chart showing an extracting process for sequence names that are not commonly included according to the embodiment of the present invention.

FIG. 22 is a flow chart showing the process at step S45 (FIG. 21) of the sequence database search result process program 12. In FIG. 22, entry names of sequences of each resultant file are input to a subroutine or the like (at step S51). i=1 is set and the number of entries of the first resultant file is set to imax (at step S52). In FIG. 20, the content of the first resultant file is displayed in the display region 21. Thus, imax=6. The contents of the second and third resultant files are displayed in the display regions 22 and 23, respectively.

Thereafter, j=2 is set (at step S53). It is determined whether or not the i-th entry name of the first resultant file is included in the j-th resultant file (at step S54). When the determined result is YES, j is incremented by "1" (j=j+1) (at step S55). Thereafter, the value of j is compared with the value of jmax (at step S56). When the value of j does not exceed the value of jmax at step S56 (the determined result at step S56 is YES), processing returns to step S54. From step S54, the same processes are repeated.

When the value of j exceeds the value of jmax at step S56 (the determined result at step S56 is NO), it is clear that the entry name is included in all the resultant files. Thus, the corresponding entry names of all the resultant files are negatively flagged so that they are not displayed in a half-tone (at step S57). Thereafter, i is incremented by "1" (i=i+1) (at step S58). Next, the value of i is compared with the value of imax (at step S59).

When the determined result at step S54 is NO, processing advances to step S58 (skipping steps S55 to S57).

When the value of i does not exceed the value of imax at step S59 (the determined result at step S59 is YES), processing returns to step S53. From step S53, the same processes are repeated. When the value of i exceeds the value of imax, the process is finished (the determined result at step S59 is NO). At step S45 of FIG. 21, entry names that are not negatively flagged from all the resultant files are displayed in a half-tone.

In the case as shown in FIG. 20, the process at step S57 is performed for entry names LOCUS 1, LOCUS 2, LOCUS 3, and LOCUS 5 corresponding to i=1, 2, 3, and 5, respectively. These entry names in the display regions 21, 22, and 23 are not displayed in a half-tone. For entry names LOCUS 4 and LOCUS 6 corresponding to i=4 and 6, respectively, the determined results at step S54 for j=3 and 2 are NO. Thus, for these entry names, the process at step S57 is not performed. In addition, the process at step S57 is not performed for entry names LOCUS 7 and LOCUS 8 which are not included in the first resultant file. Thus, only LOCUS 4, LOCUS 6, LOCUS 7, and LOCUS 8 are displayed in a half-tone.

Figure 23:
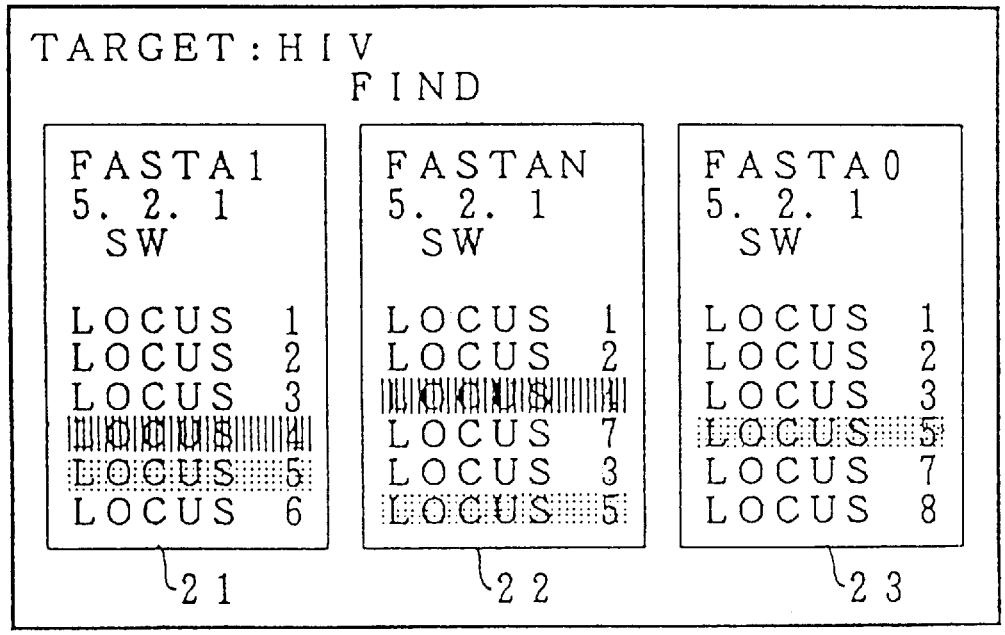
FIG. 23 is a schematic diagram showing a screen display for designated sequence names according to the embodiment of the present invention.

FIG. 23 shows a screen that displays whether or not designated sequences are included in resultant files. In FIG. 23, the user designates entry names LOCUS 4 and LOCUS 5. These entry names are displayed in respective half-tones. In such a manner, the user can designate any sequence so as to determine whether or not it is included in selected resultant files or in which resultant files it is included.

Figure 24:
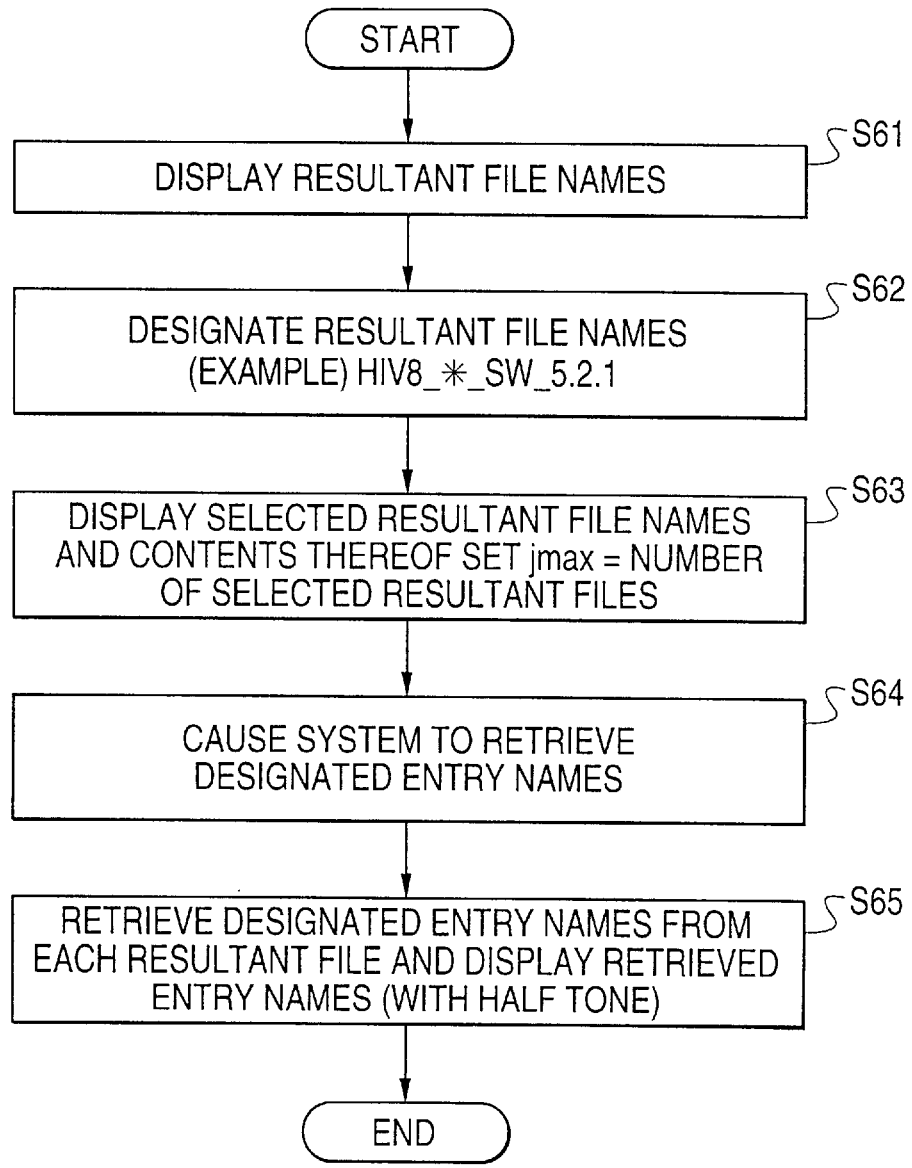
FIG. 24 is a flow chart showing a displaying process for designated sequence names according to the embodiment of the present invention.

FIG. 24 is a flow chart showing a process for selecting resultant files and a process for extracting designated entry names as shown in FIG. 23. The processes at steps S61, S62, and S63 shown in FIG. 24 are the same as those at steps S1, S2, and S3 shown in FIG. 15, respectively. After step S63, the user designates entry names of particular sequences and causes the system to retrieve the entry names from selected resultant files (at step S64). Thus, the required retrieving operation is performed and the results are displayed in a half-tone (at step S65).

FIG. 25 is a flow chart showing the process at step S65 (FIG. 24) of the sequence database search result process program 12. In FIG. 25, entry names of sequences of each resultant file are input to a subroutine or the like (at step S71). Thereafter, j=1 is set (at step S72).

Next, i=1 is set and the number of entries of the j-th resultant file is set to imax (at step S73). In FIG. 23, resultant files in the display regions 21, 22, and 23 are the first, second, and third resultant files, respectively. Since the number of entries of each of the resultant files is 6, imax is 6.

Next, it is determined whether or not the i-th entry name of the j-th resultant file is the designated entry name (at step S74). When the determined result is YES, the i-th entry name of the j-th resultant file is flagged (at step S77). j is incremented by "1" (j=j+1) (at step S78). Thereafter, the value of j is compared with the value of jmax (at step S79).

When the determined result at step S74 is NO, i is incremented by "1" (i=i+1) (at step S75). Thereafter, the value of i is compared with the value of imax (at step S76). When the value of i does not exceed the value of imax at step S76 (the determined result at step S76 is YES), processing returns to step S74. From step S74, the same processes are repeated. When the value of i exceeds the value of imax at step S76 (the determined result at step 76 is NO), processing advances to step S78.

When the value of j does not exceed the value of jmax at step S79 (the determined result at step S79 is YES), processing returns to step S73. From step S73, the same processes are repeated. When the value of j exceeds the value of jmax, the process is finished (the determined result at step S79 is NO). Thereafter, at step S65 of FIG. 24, entry names that are flagged from each resultant file are displayed in a half-tone.

In the case as shown in FIG. 23, the user designates an entry name LOCUS 4. In the case of j=1 and i=4 and the case of j=2 and i=3, the process at step S77 is performed. Thus, the entry name LOCUS 4 in the display regions 21 and 22 are displayed in a half-tone. Thereafter, the user designates an entry name LOCUS 5. In the case of j=1 and i=5, the case of j=2 and i=6, and the case of j=3 and i=4, the process at step S77 is performed. The entry name LOCUS 5 in the display regions 21, 22, and 23 are displayed in another half-tone. For other entry names, since the determined result at step S74 is NO, the process at step S77 is not performed. Thus, these other entry names are not displayed in a half-tone.

Figures 26A, 26B:
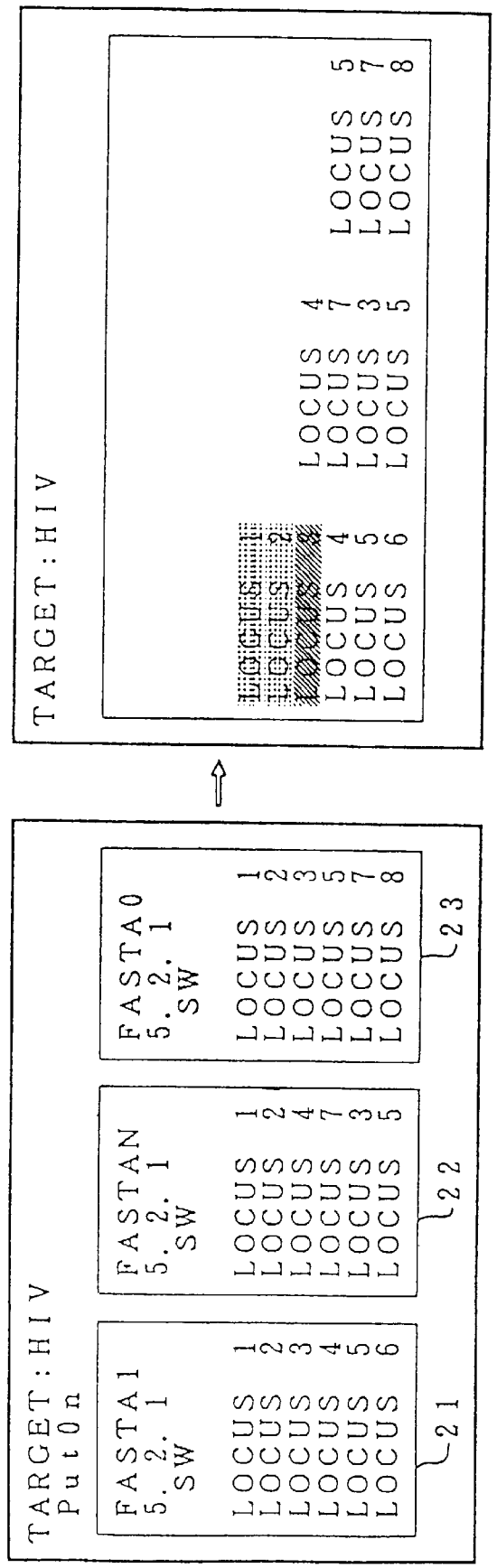
FIG. 26A is a schematic diagram showing a screen display before displaying common sequence names each in the same order according to the embodiment of the present invention.
FIG. 26B is a schematic diagram showing a screen display that has displayed common sequence names each in the same order according to the embodiment of the present invention.

FIGS. 26A and 26B show screens that highlight common parts of similarities of data from selected resultant files having similarities between them. In FIG. 26A, entry names LOCUS 1 and LOCUS 2 are displayed at the first and second entry name positions, respectively in all the display regions. On the other hand, an entry name LOCUS 3 is displayed at the third entry name positions only in the display regions 21 and 23. Thus, when the user causes the system to overlap all data of selected resultant files, as shown in FIG. 26B, LOCUS 1 and LOCUS 2 are displayed in the same half-tone and LOCUS 3 is displayed in another half-tone. Since the other entry names are not overlapped in the resultant files, they are not displayed in a half-tone, but are individually displayed. As an entry name is repeatedly overlapped, the reliability of the order thereof is high. Thus, the reliability of homology of retrieved results is shown.

FIG. 27 is a flow chart showing a process for selecting resultant files and a process for extracting similarities as shown in FIG. 26B. The processes at steps S81, S82, and S83 shown in FIG. 27 are the same as those at steps S1, S2, and S3 shown in FIG. 15, respectively. After step S83, when the user causes the system to overlap data (at step S84), the number of the same entry names at the same position in the lists of the resultant files is obtained (at step S85). The entry name is displayed in a half-tone corresponding to the obtained number (at step S86).

Figure 28:
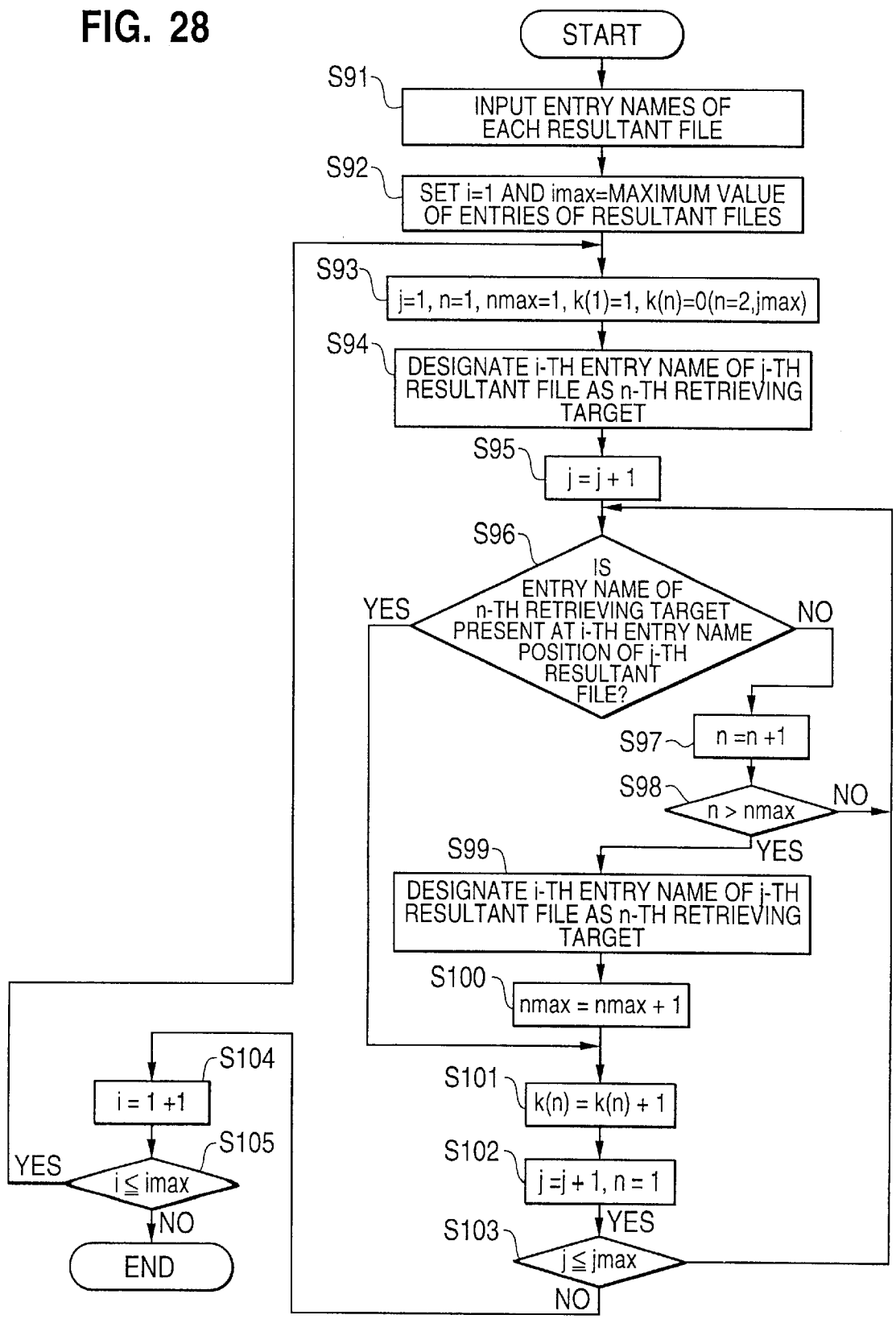
FIG. 28 is a flow chart showing an extracting process for common sequence names each in the same order according to the embodiment of the present invention.

FIG. 28 is a flow chart showing the process at step S85 (FIG. 27) of the sequence database search result process program 12. In FIG. 28, entry names of sequences of each resultant file are input to a subroutine or the like (at step S91). i=1 is set and the maximum value of the number of entries of the resultant files is set to imax (at step S92). In the case as shown in FIG. 26A, since the number of entries of each of the resultant files is 6, imax=6. The resultant files displayed in the display regions 21, 22, and 23 are first, second, and third resultant files, respectively.

Next, j=1, n=1, nmax=1, k(1)=1, and k(n)=0 (where n=2, . . . , jmax) are set (at step S93). The i-th entry name of the j-th resultant file is retrieved as the n-th retrieving target (at step S94). Next, j is incremented by "1" (j=j+1) (at step S95). It is determined whether or not the entry name retrieved as an n-th retrieving target accords with the i-th entry name of the j-th resultant file (at step S96). When the determined result is NO, n is incremented by "1" (n=n+1) (at step S97). Thereafter, the value of n is compared with the value of nmax (at step S98). When the value of n does not exceed the value of nmax (the determined result at step S98 is NO), processing returns to step S96. From step S96, the same processes are repeated.

When the value of n does exceed the value of nmax at step S98 (the determined result at step S98 is YES), the i-th entry name of the j-th is retrieved as the n-th retrieving target (at step S99). Thereafter, nmax is incremented by "1" (nmax= nmax +1) (at step S100). k(n) is incremented by "1" (k(n) =k(n)+1) (at step S101). j is incremented by "1" (j=j+1) and n=1 is set (at step S102). Thereafter, the value of j is compared with the value of jmax (at step S103).

When the determined result at step S96 is YES, processing advances to step S101 (skipping steps S97 to S100).

When the value of j does not exceed the value of jmax at step S103 (the determined result at step S103 is YES), processing returns to step S96. From step S96, the same processes are repeated. When the value of j exceeds the value of jmax at step S103 (the determined result at step S103 is NO), i is incremented by "1" (i=i+1) (at step S104). Thereafter, the value of i is compared with the value of imax (at step S105).

When the value of i does not exceed the value of imax at step S105 (the determined result at step S105 is YES), processing returns to step S93. From step S93, the same processes are repeated. When the value of i exceeds the value of imax, the process is finished (the determined result at step S105 is NO). At step S86 of FIG. 27, entry names retrieved as the n-th retrieving targets are displayed from the left at each order of score, in a half-tone corresponding to the value of k(n). The half-tones used for entry names are predetermined using environmental variables.

In the case as shown in FIG. 26A, for i=1, since the same entry name LOCUS 1 is included in three resultant files, entry names are retrieved only for n=1. For j=2 and 3, the determined results at step S96 are YES. Thus, since k(1) corresponding to LOCUS 1 is incremented twice (namely, by "2") (at step S101), k(1) becomes 3. This applies to the case of i=2.

For i=3, the third entry name LOCUS 3 of the first resultant file is retrieved as the first retrieving target (at step S94). Since LOCUS 3 is not present at the third entry name position of the second resultant file (the determined result at step S96 is NO), the third entry name LOCUS 4 of the second resultant file is retrieved as the second retrieving target (at step S99). Thus, k(2) corresponding to LOCUS 4 is incremented by "1" (at step S101). Since LOCUS 3 is present at the third entry name position of the third resultant file (the determined result at step S96 is YES), k(1) corresponding to LOCUS 3 is incremented by "1" and becomes 2 (at step S101). Since j=4>3=jmax (the determined result at step S103 is NO), i is incremented by "1".

For i=4, the fourth entry name LOCUS 4 of the first resultant file is retrieved as the first retrieving target (at step S94). Since LOCUS 4 is not present at the fourth entry name position of the second resultant file (the determined result at step S96 is NO), the fourth entry name LOCUS 7 of the second resultant file is retrieved as the second retrieving target (at step S99). k(2) corresponding to LOCUS 7 is incremented by "1" (at step S101).

Since neither LOCUS 4 nor LOCUS 7 is present at the fourth entry name position of the third resultant file (the determined result at step S96 is NO), the fourth entry name LOCUS 5 of the third resultant file is retrieved as the third retrieving target (at step S99). k(3) corresponding to LOCUS 5 is incremented by "1" (at step S101). Since j=4 (at step S102), i is incremented by "1". However, since k(1) corresponding to LOCUS 5 is not incremented, it is still 1 (at step S93). This process applies to the cases of i=5 and 6.

At step S86 of FIG. 27, the related entry names are displayed in half-tones corresponding to values of k(n) as shown in FIG. 26B. However, entry names for k(n)=1 are not displayed in a half-tone.

Figures 29A, 29B:
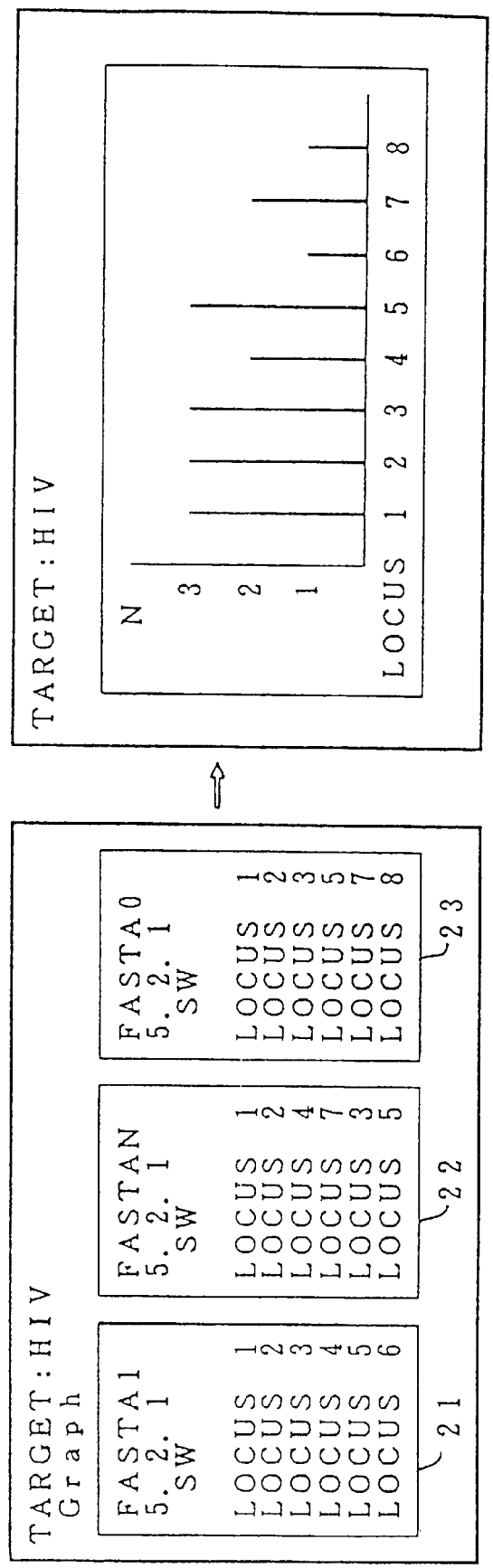
FIG. 29A is a schematic diagram showing a screen display before displaying a graph according to the embodiment of the present invention.
FIG. 29B is a schematic diagram showing a screen display that has displayed a graph of the number of sequence names according to the embodiment of the present invention.

FIGS. 29A and 29B show an example of a graphical displays of the number of sequences in selected resultant files. In FIG. 29A, when the user instructs the system to display a graph, the number N of each entry name included in all the resultant files is graphically displayed as shown in FIG. 29B. When the same entry name is included in many resultant files, the similarity thereof to a sequence to be retrieved is considered to be high. Thus, when the numbers of entry names are graphically displayed, the reliability of retrieved results is shown. For example, LOCUS 4, LOCUS 5, and LOCUS 7 are not highlighted in the overlap display as shown in FIG. 26B. However, in FIG. 29B, it is clear that they appear several times in the display regions 21, 22, and 23.

Figure 30:
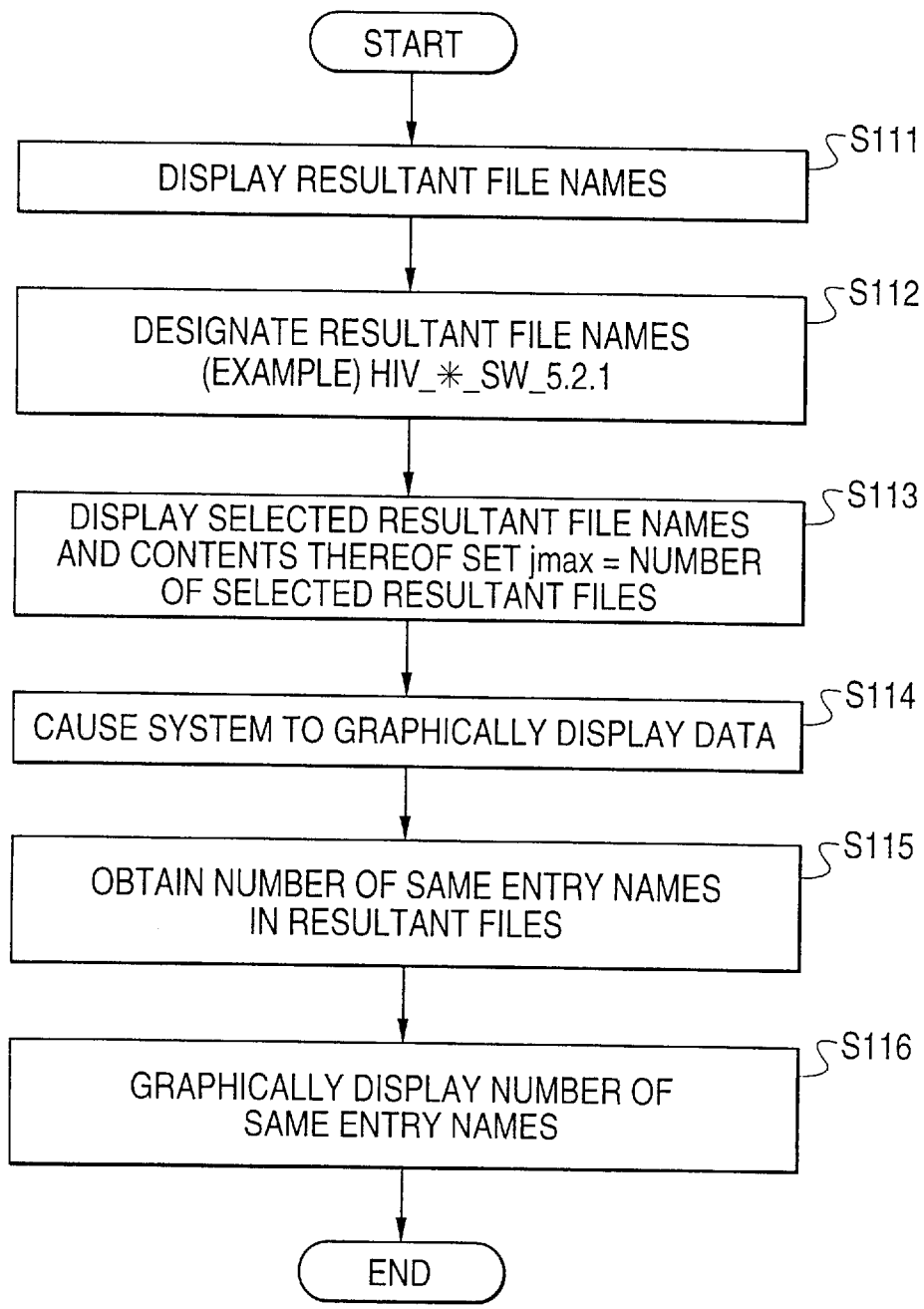
FIG. 30 is a flow chart showing a graph displaying process for the number of sequence names according to the embodiment of the present invention.

FIG. 30 is a flow chart showing a process for selecting resultant files and a process for graphically displaying data as shown in FIG. 29B. The processes at steps S111, S112, and S113 shown in FIG. 30 are the same as those at steps S1, S2, and S3 shown in FIG. 15, respectively. After step S113, when the user causes the system to graphically display data (at step S114), the total number of the same entry names in the resultant files is obtained (at step S115). The number of the same entry names is graphically displayed (at step S116).

Figure 31:
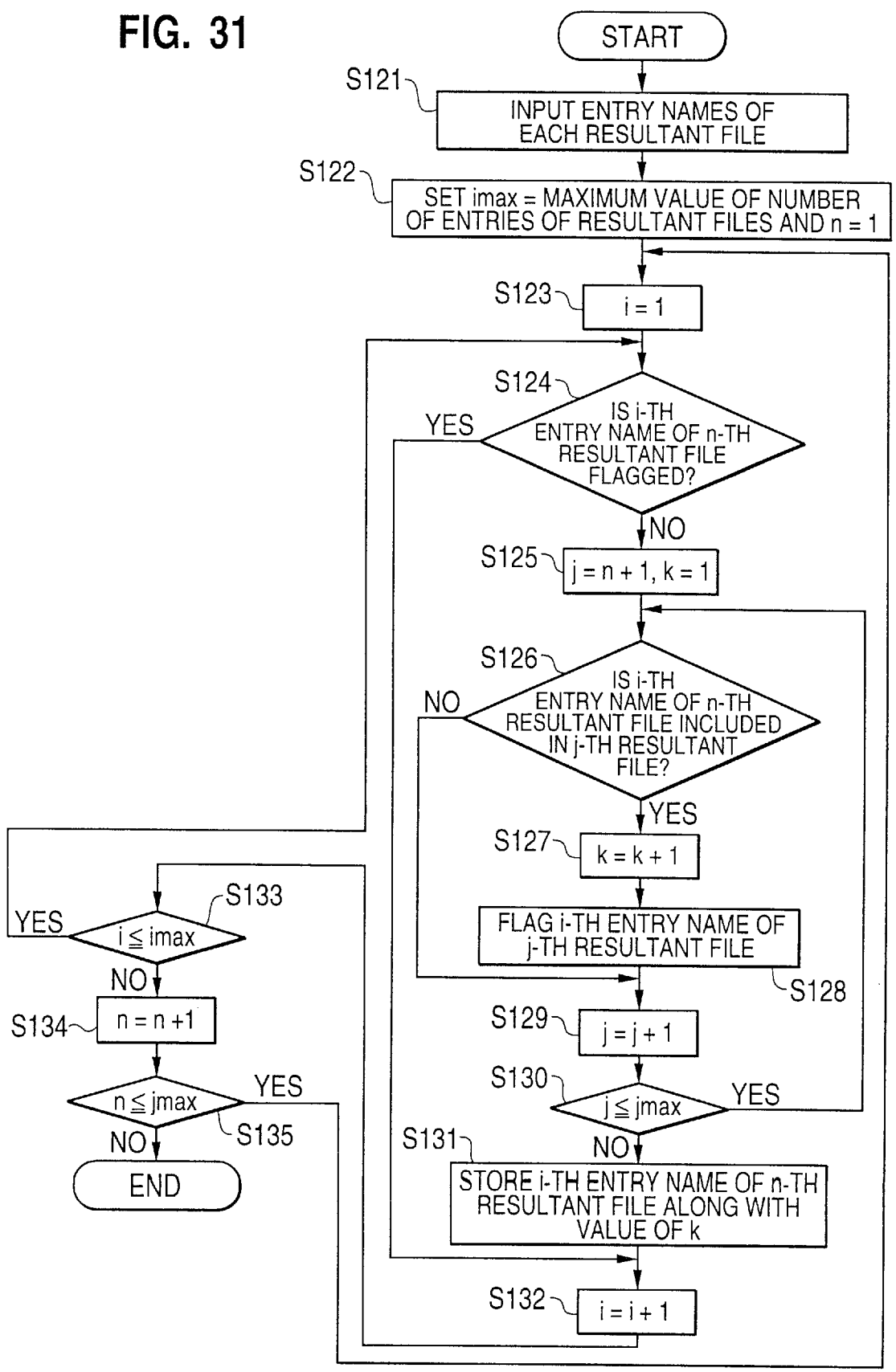
FIG. 31 is a flow chart showing a calculating process for the number of sequence names according to the embodiment of the present invention.

FIG. 31 is a flow chart showing the process at step S115 (FIG. 30) of the sequence database search result process program 12. In FIG. 31, entry names of sequences of each resultant file are input to a subroutine or the like (at step S121). The maximum value of the number of entries of the resultant files is set to imax and n=1 is set (at step S122). In the case as shown in FIG. 29A, imax=6. The resultant files displayed in the display regions 21, 22, and 23 are first, second, and third resultant files, respectively.

Next, i=1 is set (at step S123). It is determined whether or not the i-th entry name of the n-th resultant file is flagged. When the determined result is NO, j=n+1 and k=1 are set (at step S125). Thereafter, it is determined whether or not the i-th entry name of the n-th resultant file is included in the j-th resultant file (at step S126). When the determined result is YES, k=k+1 is set (at step S127). The i-th entry name of the j-th resultant file is flagged (at step S128). Next, j is incremented by "1" (at step S129). The value of j is compared with the value of jmax (at step S130).

When the determined result at step S126 is NO, processing advances to step S129.

When the value of j does not exceed the value of jmax at step S130 (the determined result at step S130 is YES), processing returns to step S126. From step S126, the same processes are repeated. When the value of j exceeds the value of jmax (the determined result at step S130 is NO), the i-th entry name of the n-th resultant file is stored in a memory (not shown) along with the value of k (at step S131). Thereafter, i is incremented by "1" (at step S132). The value of i is compared with the value of imax (at step S133). When the determined result at step S124 is YES, processing advances to step S132.

When the value of i does not exceed the value of imax at step S133 (the determined result at step S133 is YES), processing returns to step S124. From step S124, the same processes are repeated. When the value of i exceeds the value of imax, n is incremented by "1" (at step S134). The value of n is compared with the value of jmax (at step S135).

When the value of n does not exceed the value of jmax at step S135 (the determined result at step S135 is YES), processing returns to step S123. From step S123, the same processes are repeated. When the value of n exceeds the value of jmax, the process is finished (the determined result at step S135 is NO). Thereafter, at step S116 shown in FIG. 30, each entry name and the value of k thereof are retrieved from the memory in succession and the values of k are graphically displayed as the number of entry names.

In the case as shown in FIG. 29A, for n=1 and i=1, since the fist entry name LOCUS 1 of the first resultant file is included in both the second and third resultant files (the determined result at step S126 is YES), for j=2 and 3, k is incremented by "1" (at step S127). LOCUS 1 of the second and third resultant files is flagged (at step S128). At this point, k=3 is stored as the number of entry name LOCUS 1 (at step S131). This process applies to the cases of LOCUS 2, LOCUS 3, and LOCUS 5 corresponding to i=2, 3, and 5, respectively.

For i=4, the fourth entry name LOCUS 4 of the first resultant file is included in the second resultant file (the determined result at step S126 is YES). However, LOCUS 4 is not included in the third resultant file (the determined result at step S126 is NO). Thus, for only j=2, k is incremented by "1" (at step S127). LOCUS 4 of the second resultant file is flagged (at step S128). At this point, k=2 is stored as the number of entry name LOCUS 4 (at step S131).

For i=6, the sixth entry name LOUCS 6 of the first resultant file is not included in other resultant files (the determined result at step S126 is NO). Thus, k is not incremented and k=1 is stored as the number of entry name LOCUS 6 (at step S131).

Next, i is incremented by "1" (at step S132). Thus, the value of i exceeds the value of imax (the determined result at step S133 is NO). n is incremented by "1" and becomes 2 (at step S134). Thus, processing returns to step S123. From step S123, the same processes are repeated. For i=1, 2, 3, 5, or 6, the entry name has been flagged (the determined result at step S124 is YES). Thus, k is not incremented and the process at step S131 is not performed.

For i=4, the fourth entry name LOCUS 7 of the second resultant file has not been flagged (the determined result at step S124 is NO). In addition, LOCUS 7 is included in the third resultant file (the determined result at step S126 is YES). For j=3, k is incremented by "1" (at step S127). LOCUS 7 of the third resultant file is flagged (at step S128). At this point, k=2 is stored as the number of entry name LOCUS 7 (at step S131).

For n=3, the determination at step 8 is performed for the entry name LOCUS 8 for i=6. However, since the fourth resultant file is not present (the determined result at step S126 is NO), k is not incremented. Thus, k=1 is stored as the number of entry name LOCUS 8 (at step S131).

The numbers of entry names stored are graphically displayed as shown in FIG. 29B (at step S116).

In the above-described embodiment, examples of extracted features of selected resultant files are shown. However, the present invention is not limited to such examples. Instead, when another application is provided as the sequence database search result process program 12, other features can be extracted.

In FIGS. 13, 14, and so forth, file names and entry names are displayed in a half-tone. However, they can be displayed with multiple color markers or gray scale markers. In the present invention, since the retrieved results of the resultant files are used for analysis data such as comparison, alignment, and so forth, a whole resultant file, or only marked sequence information, or only non-marked sequence information, can be stored by choice.

In addition, the present invention is not limited to the process of sequence database search results in the biotechnology field. Instead, the present invention can be applied to a process for extracting arbitrary features among a plurality of lists having any data items sequentially arranged.

According to the present invention, as seen in the sequence database search results, a plurality of lists having similarities and differences can be effectively compared. In the case of the sequence database search results, a large number of lists including a huge number of sequence names can be quickly compared.

When a plurality of lists are compared and their similarities are extracted, data having high reliability can be obtained. As the sequence database search results, data such as sequence names included in many lists can be effectively extracted.

In addition, since the various features extracted are clearly displayed on the screen, they can be easily understood. By selecting and storing the features, they can be easily supplied to another system or to another apparatus.

Moreover, since files that store the sequence database search results are managed with item names such as method for searching, particular files with a particular item name or parameter can be easily selected from many files.

Although the present invention has been shown and described with respect to a best mode embodiment thereof, it should be understood by those skilled in the art that the foregoing and various other changes, omissions, and additions in the form and detail thereof may be made therein without departing from the spirit and scope of the present invention.

What is claimed is:

1. A list processing system for use in an information processing apparatus for processing data stored in a database, comprising:
   search means for searching data similar to given data based on a similarity calculated between the given data and data in the database;
   list storing means for storing a plurality of lists, each of which includes a plurality of data and represents a search result of a search in the database, at least a piece of the data in one of the lists being included in another one of the lists; and
   feature extracting means for extracting a feature representing a relation among the data in the lists stored in said list storing means as information used to obtain similar data with a high similarity.

2. The list processing system as set forth in claim 1, wherein said list storing means is adapted for storing the lists, at least one of which having the data arranged in a certain order.

3. The list processing system as set forth in claim 2, wherein said list storing means is adapted for storing a file name of at least one of the lists, the file name including information used to arrange the data in the certain order.

4. The list processing system as set forth in claim 1, further comprising feature displaying means for displaying the feature extracted by said feature extracting means.

5. A list processing system for use with a sequence database search apparatus for searching sequence data stored in a database and outputting an identifier of sequence data similar to given sequence data, comprising:
   search means searching sequence data similar to the given sequence data based on a similarity calculated between the given sequence data and sequence data in the database;
   list storing means for storing a plurality of lists each having identifiers of a plurality of similar sequence data, at least one of the identifiers in one of the lists being included in another one of the lists; and
   feature extracting means for extracting a feature representing a relation among the identifiers in the lists stored in said list storing means as information used to obtain similar sequence data with a high similarity.

6. The list processing system as set forth in claim 5, wherein said list storing means is adapted for storing the lists, at least one of which having the identifiers of the similar data arranged in a certain order.

7. The list processing system as set forth in claim 6, wherein said list storing means is adapted for storing a file name of at least one of the lists, the file name including information used to arrange the identifiers in the certain order.

8. The list processing system as set forth in claim 7, wherein said list storing means is adapted for storing the file name, including at least one of an identification name of the given data, an identification name of a technique that is used to arrange the identifiers in the certain order, an identification name of the database, and a parameter of the technique so as to manage the lists.

9. The list processing system as set forth in claim 5, wherein said feature extracting means is adapted for extracting one of a similarity and a difference among the lists as the feature.

10. The list processing system as set forth in claim 5, wherein said feature extracting means is adapted for extracting an identifier that is commonly included in the lists as the feature.

11. The list processing system as set forth in claim 5, wherein said feature extracting means is adapted for extracting an identifier that is not commonly included in the lists as the feature.

12. The list processing system as set forth in claim 5, wherein said feature extracting means is adapted for extracting an identifier that is not included in a designated one of the lists as the feature.

13. The list processing system as set forth in claim 5, wherein said feature extracting means is adapted for extracting a designated identifier from the lists as the feature.

14. The list processing system as set forth in claim 5, wherein said feature extracting means is adapted for extracting an identifier in the same order that is commonly included in the lists as the feature.

15. The list processing system as set forth in claim 5, wherein said feature extracting means is adapted for extracting the number of the same identifiers that are included in the lists as the feature.

16. The list processing system as set forth in claim 5, further comprising feature displaying means for displaying the feature extracted by said feature extracting means on a screen, wherein said list storing means is adapted for storing the lists, at least one of which having the identifiers of the similar data arranged in a certain order.

17. The list processing system as set forth in claim 16, wherein said list storing means is adapted for storing a file name of at least one of the lists, the file name including information used to arrange the identifiers in the certain order, and said feature displaying means is adapted for displaying the file name and contents of a list with the file name on the screen when the file name is designated.

18. The list processing system as set forth in claim 16, wherein said feature displaying means is adapted for graphically displaying the feature.

19. A list processing method for processing data stored in a database, comprising the steps of:

searching data similar to given data based on a similarity calculated between the given data and data in the database;

storing a plurality of lists, each of which includes a plurality of data and represents a search result of a search in the database, at least a piece of the data in one of the lists being included in another one of the lists;

storing a file name of at least one of the lists, the file name including information used as a search condition to search the data in the database; and categorizing the lists according to an item of the information using the file name.

20. The list processing method as set forth in claim 19, further comprising the steps of:

arranging the data in each of the lists in a certain order; and adding the information used to arrange the data in the certain order to the file name.

21. The list processing method as set forth in claim 19, further comprising the steps of:

displaying file names of the lists stored;

selecting a plurality of file names from the displayed file names using the information; and displaying contents of lists corresponding to the plurality of file names selected.

22. The list processing method as set forth in claim 21, further comprising the steps of:

extracting a feature of the lists corresponding to the plurality of the file names selected as information used to obtain similar data with a high similarity; and displaying an extracted feature on a screen.

23. A computer-readable storage medium used to direct a computer for processing data stored in a database to perform the functions of:

storing a plurality of lists, each of which includes a plurality of data and represents a search result of a search in the database, at least a piece of the data in one of the lists being included in another one of the lists; and extracting a feature representing a relation among the data in the lists as information used to obtain similar data with a high similarity.

* * * * *

UNITED STATES PATENT AND TRADEMARK OFFICE
CERTIFICATE OF CORRECTION

PATENT NO.:   5,873,082
DATED     :   February 16, 1999
INVENTOR(S):  Tamotsu NOGUCHI It is certified that error appears in the above-identified patent and that said Letters Patent is hereby corrected as shown below:

Col. 6,    line 66, change "HIV11 FASTA SW 5.5.1" to --HIV11_FASTA_SW_5.5.1--.

Col. 16,   line 45, change "LOUCS" to --LOCUS--.

Col. 19, line 9, make "said feature displaying means..." a new paragraph.

Signed and Sealed this

Fourth Day of April, 2000

Attest:

Attesting Officer

Q. TODD DICKINSON

Director of Patents and Trademarks